US008875331B2

(12) United States Patent
Taylor

(10) Patent No.: US 8,875,331 B2
(45) Date of Patent: *Nov. 4, 2014

(54) ADAPTIVE CUSHION METHOD AND APPARATUS FOR MINIMIZING FORCE CONCENTRATIONS ON A HUMAN BODY

(71) Applicant: Stryker Corporation, Kalamazoo, MI (US)

(72) Inventor: Geoffrey L. Taylor, Winnipeg (CA)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/019,089

(22) Filed: Sep. 5, 2013

(65) Prior Publication Data
US 2014/0026327 A1 Jan. 30, 2014

Related U.S. Application Data

(63) Continuation of application No. 12/075,937, filed on Mar. 15, 2008, now Pat. No. 8,533,879.

(51) Int. Cl.
| A47C 27/08 | (2006.01) |
|---|---|
| G01L 1/18 | (2006.01) |
| A47C 27/10 | (2006.01) |
| A61B 5/00 | (2006.01) |
| G01L 1/20 | (2006.01) |
| A61B 5/11 | (2006.01) |

(52) U.S. Cl.
CPC ............... *A47C 27/083* (2013.01); *G01L 1/18* (2013.01); *A47C 27/10* (2013.01); *A61B 5/6892* (2013.01); *A61B 5/6887* (2013.01); *G01L 1/205* (2013.01); *A61B 5/1126* (2013.01); *A61B 2562/0252* (2013.01); *A61B 2562/0247* (2013.01); *A61B 2562/046* (2013.01); *A47C 27/082* (2013.01)
USPC ........................... 5/713; 5/600; 5/613; 5/690

(58) Field of Classification Search
USPC ..................................... 5/600, 613, 690, 713
See application file for complete search history.

(56) References Cited

U.S. PATENT DOCUMENTS

| 3,818,756 | A | * | 6/1974 | Barron et al. | .................... 73/172 |
|---|---|---|---|---|---|
| 3,818,758 | A | * | 6/1974 | Easter | ......................... 73/204.12 |
| 3,996,922 | A | * | 12/1976 | Basham | ........................ 600/535 |
| 4,033,332 | A | * | 7/1977 | Hardway et al. | .............. 600/535 |
| 4,257,728 | A | * | 3/1981 | Schmidt et al. | ............... 414/468 |
| 4,267,728 | A | * | 5/1981 | Manley et al. | .................. 73/172 |
| 4,308,872 | A | * | 1/1982 | Watson et al. | ................ 600/538 |
| 4,438,771 | A | * | 3/1984 | Friesen et al. | ................ 600/484 |

(Continued)

*Primary Examiner* — Robert G Santos
*Assistant Examiner* — David E Sosnowski
(74) *Attorney, Agent, or Firm* — Warner Norcross & Judd LLP

(57) ABSTRACT

An adaptive cushion for reducing pressure on body parts of a person positioned on a chair or bed includes an overlay cushion having a plurality of individual air bladder cells, each having thereon a force sensor. The cushion includes a controller for inflating and deflating individual air bladder cells to air pressures that tend to reduce the interface pressures sensed by the force sensors. A pressure reduction method includes varying the inflation pressure in a first air bladder cell while measuring the sum of the interface pressures exerted on all or a plurality of the air bladder cells, re-pressurizing the first cell to that air pressure for which a minimum total interface pressure was obtained, repeating this process for the remaining air bladder cells.

23 Claims, 11 Drawing Sheets

(56) References Cited

U.S. PATENT DOCUMENTS

| | | | |
|---|---|---|---|
| 4,509,527 A * | 4/1985 | Fraden | 600/484 |
| RE32,180 E * | 6/1986 | Lewiner et al. | 340/573.1 |
| 4,633,237 A * | 12/1986 | Tucknott et al. | 340/573.4 |
| 4,657,026 A * | 4/1987 | Tagg | 600/534 |
| 4,738,266 A * | 4/1988 | Thatcher | 600/473 |
| 4,827,763 A * | 5/1989 | Bourland et al. | 73/172 |
| 4,986,277 A * | 1/1991 | Sackner | 600/485 |
| 5,002,060 A * | 3/1991 | Nedivi | 600/484 |
| 5,010,772 A * | 4/1991 | Bourland et al. | 73/862.046 |
| 5,025,795 A * | 6/1991 | Kunig | 600/526 |
| 5,060,174 A * | 10/1991 | Gross | 702/139 |
| 5,062,169 A * | 11/1991 | Kennedy et al. | 5/713 |
| 5,128,880 A * | 7/1992 | White | 382/165 |
| 5,178,151 A * | 1/1993 | Sackner | 600/485 |
| 5,184,112 A * | 2/1993 | Gusakov | 340/573.1 |
| 5,209,126 A * | 5/1993 | Grahn | 73/862.046 |
| 5,253,656 A * | 10/1993 | Rincoe et al. | 600/595 |
| 5,276,432 A * | 1/1994 | Travis | 340/573.4 |
| 5,448,996 A * | 9/1995 | Bellin et al. | 600/574 |
| 5,471,198 A * | 11/1995 | Newham | 340/573.4 |
| 5,479,932 A * | 1/1996 | Higgins et al. | 600/529 |
| 5,571,142 A * | 11/1996 | Brown et al. | 607/5 |
| 5,590,650 A * | 1/1997 | Genova | 600/301 |
| 5,600,108 A * | 2/1997 | Newham | 200/50.28 |
| 5,623,760 A * | 4/1997 | Newham | 29/622 |
| 5,633,627 A * | 5/1997 | Newham | 340/573.4 |
| 5,640,145 A * | 6/1997 | Newham | 340/573.1 |
| 5,654,694 A * | 8/1997 | Newham | 340/573.1 |
| 5,684,460 A * | 11/1997 | Scanlon | 340/573.1 |
| 5,722,287 A * | 3/1998 | Forstein | 73/172 |
| 5,800,360 A * | 9/1998 | Kisner et al. | 600/532 |
| 5,865,755 A * | 2/1999 | Golub | 600/485 |
| 5,964,720 A * | 10/1999 | Pelz | 600/595 |
| 5,967,979 A * | 10/1999 | Taylor et al. | 600/407 |
| 5,993,400 A * | 11/1999 | Rincoe et al. | 600/595 |
| 6,011,477 A * | 1/2000 | Teodorescu et al. | 340/573.1 |
| 6,025,782 A * | 2/2000 | Newham | 340/573.1 |
| 6,047,203 A * | 4/2000 | Sackner et al. | 600/388 |
| 6,147,592 A * | 11/2000 | Ulrich et al. | 340/286.07 |
| 6,155,120 A * | 12/2000 | Taylor | 73/862.046 |
| 6,180,893 B1 * | 1/2001 | Salgo | 177/144 |
| 6,216,545 B1 * | 4/2001 | Taylor | 73/862.046 |
| 6,279,183 B1 * | 8/2001 | Kummer et al. | 5/600 |
| 6,280,392 B1 * | 8/2001 | Yoshimi et al. | 600/534 |
| 6,297,738 B1 * | 10/2001 | Newham | 340/573.1 |
| 6,307,168 B1 * | 10/2001 | Newham | 200/86 R |
| D451,604 S * | 12/2001 | Kasabach et al. | D24/186 |
| 6,341,504 B1 * | 1/2002 | Istook | 66/172 E |
| 6,377,177 B1 * | 4/2002 | Broussard et al. | 340/573.1 |
| 6,396,004 B2 * | 5/2002 | Salgo | 177/144 |
| 6,413,225 B1 * | 7/2002 | Sackner et al. | 600/529 |
| 6,447,457 B1 * | 9/2002 | Forstner et al. | 600/485 |
| 6,450,957 B1 * | 9/2002 | Yoshimi et al. | 600/309 |
| 6,468,234 B1 * | 10/2002 | Van der Loos et al. | 600/595 |
| 6,478,744 B2 * | 11/2002 | Mohler | 600/485 |
| 6,485,441 B2 * | 11/2002 | Woodward | 600/595 |
| 6,491,647 B1 * | 12/2002 | Bridger et al. | 600/585 |
| 6,493,568 B1 * | 12/2002 | Bell et al. | 600/323 |
| 6,498,652 B1 * | 12/2002 | Varshneya et al. | 356/477 |
| 6,524,239 B1 * | 2/2003 | Reed et al. | 600/300 |
| 6,543,299 B2 * | 4/2003 | Taylor | 73/862.046 |
| 6,546,813 B2 * | 4/2003 | Hubbard, Jr. | 73/862.041 |
| 6,547,743 B2 * | 4/2003 | Brydon | 600/534 |
| 6,551,251 B2 * | 4/2003 | Zuckerwar et al. | 600/528 |
| 6,551,252 B2 * | 4/2003 | Sackner et al. | 600/536 |
| 6,577,897 B1 * | 6/2003 | Shurubura et al. | 600/547 |
| 6,585,328 B1 * | 7/2003 | Oexman et al. | 700/117 |
| 6,647,289 B2 * | 11/2003 | Prutchi | 600/547 |
| 6,684,418 B2 * | 2/2004 | Choi | 4/483 |
| 6,685,635 B2 * | 2/2004 | Shani et al. | 600/306 |
| 6,698,046 B1 * | 3/2004 | Wu | 5/713 |
| 6,721,980 B1 * | 4/2004 | Price et al. | 5/713 |
| 6,829,501 B2 * | 12/2004 | Nielsen et al. | 600/513 |
| 6,840,117 B2 * | 1/2005 | Hubbard, Jr. | 73/862.041 |
| 6,840,907 B1 * | 1/2005 | Brydon | 600/534 |
| 6,921,365 B2 * | 7/2005 | Lee | 600/300 |
| 6,932,774 B2 * | 8/2005 | Nakatani et al. | 600/534 |
| 7,001,334 B2 * | 2/2006 | Reed et al. | 600/300 |
| 7,030,764 B2 * | 4/2006 | Smith et al. | 340/573.1 |
| 7,054,679 B2 * | 5/2006 | Hirsh | 600/523 |
| 7,065,396 B2 * | 6/2006 | Hampton | 600/509 |
| 7,076,371 B2 * | 7/2006 | Fu | 702/19 |
| 7,125,383 B2 * | 10/2006 | Hoctor et al. | 600/438 |
| 7,155,273 B2 * | 12/2006 | Taylor | 600/476 |
| 7,155,281 B1 * | 12/2006 | Fayram | 607/19 |
| 7,173,437 B2 * | 2/2007 | Hervieux et al. | 324/663 |
| 7,201,063 B2 * | 4/2007 | Taylor | 73/841 |
| 7,204,808 B1 * | 4/2007 | Friedman et al. | 600/490 |
| 7,211,053 B2 * | 5/2007 | Marmaropoulos et al. | 600/587 |
| 7,245,958 B1 * | 7/2007 | Navab et al. | 600/407 |
| 7,282,654 B2 * | 10/2007 | Salgo et al. | 177/144 |
| 7,319,386 B2 * | 1/2008 | Collins et al. | 340/539.12 |
| 7,330,127 B2 * | 2/2008 | Price et al. | 340/666 |
| 7,437,787 B2 * | 10/2008 | Bhai | 5/613 |
| 7,459,645 B2 * | 12/2008 | Skinner et al. | 177/144 |
| 7,480,953 B2 * | 1/2009 | Romano et al. | 5/714 |
| 7,500,280 B2 * | 3/2009 | Dixon et al. | 5/713 |
| 7,515,059 B2 * | 4/2009 | Price et al. | 340/666 |
| 7,557,718 B2 * | 7/2009 | Petrosenko et al. | 340/573.1 |
| 7,568,246 B2 * | 8/2009 | Weismiller et al. | 5/424 |
| 7,631,557 B2 * | 12/2009 | DeBeliso et al. | 73/379.02 |
| 7,646,294 B2 * | 1/2010 | Kow et al. | 340/525 |
| 7,656,299 B2 * | 2/2010 | Gentry et al. | 340/573.1 |
| 7,657,956 B2 * | 2/2010 | Stacy et al. | 5/713 |
| 7,699,784 B2 * | 4/2010 | Wan Fong et al. | 600/481 |
| 2003/0004423 A1 * | 1/2003 | Lavie et al. | 600/500 |
| 2004/0087865 A1 * | 5/2004 | Kelly | 600/508 |
| 2004/0167418 A1 * | 8/2004 | Nguyen et al. | 600/513 |
| 2004/0186380 A1 * | 9/2004 | Kristiansen | 600/447 |
| 2004/0210155 A1 * | 10/2004 | Takemura et al. | 600/534 |
| 2005/0075542 A1 * | 4/2005 | Goldreich | 600/300 |
| 2005/0101875 A1 * | 5/2005 | Semler et al. | 600/509 |
| 2005/0124864 A1 * | 6/2005 | Mack et al. | 600/300 |
| 2005/0171443 A1 * | 8/2005 | Gorenberg et al. | 600/490 |
| 2005/0190068 A1 * | 9/2005 | Gentry et al. | 340/665 |
| 2005/0245839 A1 * | 11/2005 | Stivoric et al. | 600/549 |
| 2006/0028350 A1 * | 2/2006 | Bhai | 340/666 |
| 2006/0065060 A1 * | 3/2006 | Ito et al. | 73/862.046 |
| 2006/0066449 A1 * | 3/2006 | Johnson | 340/539.12 |
| 2006/0100530 A1 * | 5/2006 | Kliot et al. | 600/483 |
| 2006/0100534 A1 * | 5/2006 | Colombo et al. | 600/513 |
| 2006/0129047 A1 * | 6/2006 | Ruotoistenmaki | 600/483 |
| 2006/0173363 A1 * | 8/2006 | Felder et al. | 600/485 |
| 2006/0195035 A1 * | 8/2006 | Sun | 600/503 |
| 2006/0224072 A1 * | 10/2006 | Shennib | 600/509 |
| 2006/0224076 A1 * | 10/2006 | Lange et al. | 600/529 |
| 2006/0241510 A1 * | 10/2006 | Halperin et al. | 600/534 |
| 2006/0258914 A1 * | 11/2006 | Derchak et al. | 600/300 |
| 2006/0264767 A1 * | 11/2006 | Shennib | 600/509 |
| 2007/0083098 A1 * | 4/2007 | Stern et al. | 600/407 |
| 2007/0118054 A1 * | 5/2007 | Pinhas et al. | 600/587 |
| 2007/0149883 A1 * | 6/2007 | Yesha | 600/485 |
| 2007/0156031 A1 * | 7/2007 | Sullivan et al. | 600/300 |
| 2008/0065060 A1 * | 3/2008 | Ein-Gal | 606/34 |
| 2009/0056020 A1 * | 3/2009 | Caminade et al. | 5/600 |
| 2009/0056027 A1 * | 3/2009 | Ball et al. | 5/690 |
| 2009/0093912 A1 * | 4/2009 | Wilker, Jr. | 700/282 |
| 2009/0093990 A1 * | 4/2009 | McGuire et al. | 702/139 |
| 2009/0099480 A1 * | 4/2009 | Salgo et al. | 600/595 |
| 2009/0183312 A1 * | 7/2009 | Price et al. | 5/706 |
| 2010/0045454 A1 * | 2/2010 | Knight et al. | 340/521 |
| 2010/0094139 A1 * | 4/2010 | Brauers et al. | 600/484 |
| 2010/0308846 A1 * | 12/2010 | Camus | 324/679 |
| 2011/0068939 A1 * | 3/2011 | Lachenbruch | 340/626 |

\* cited by examiner

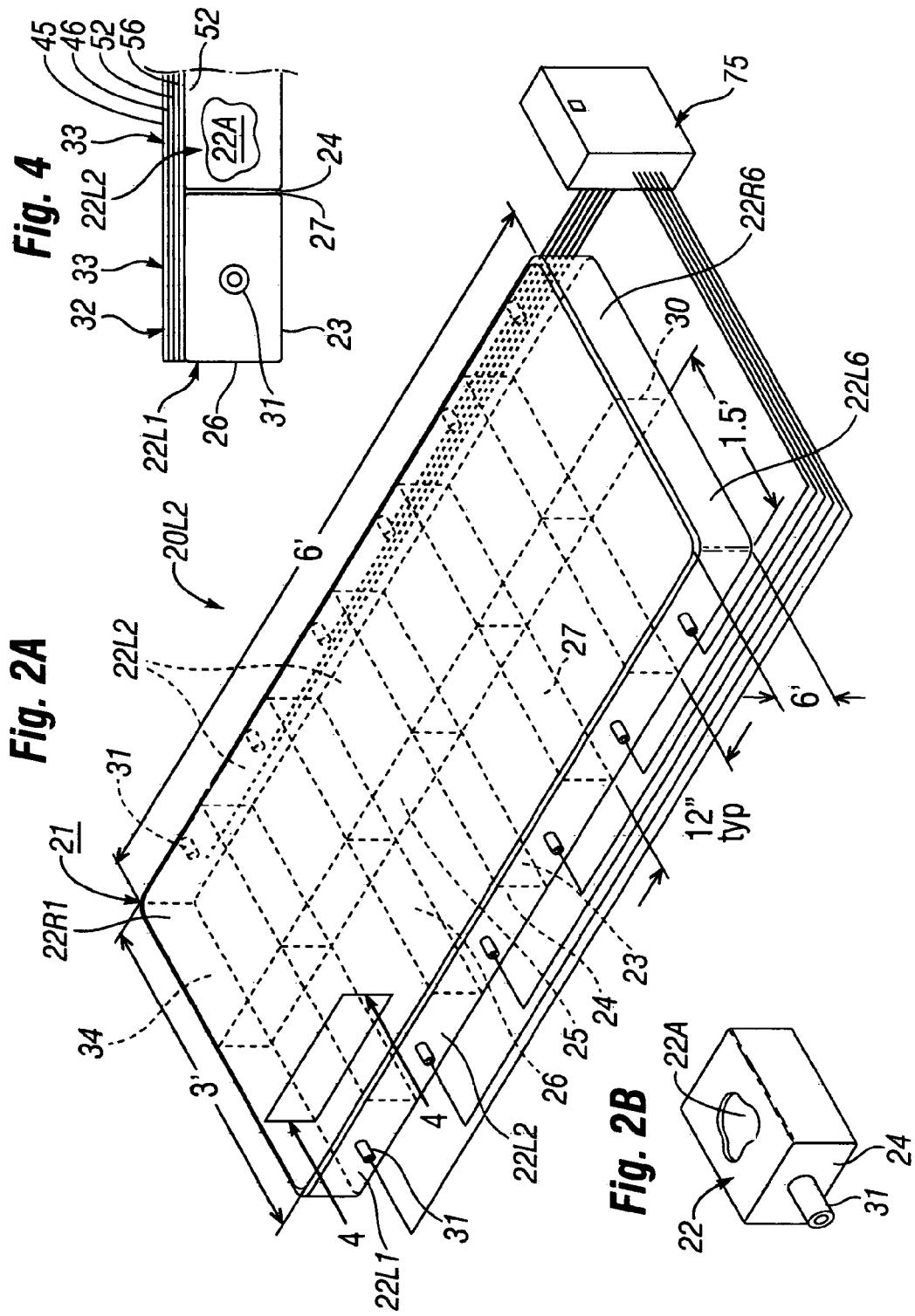

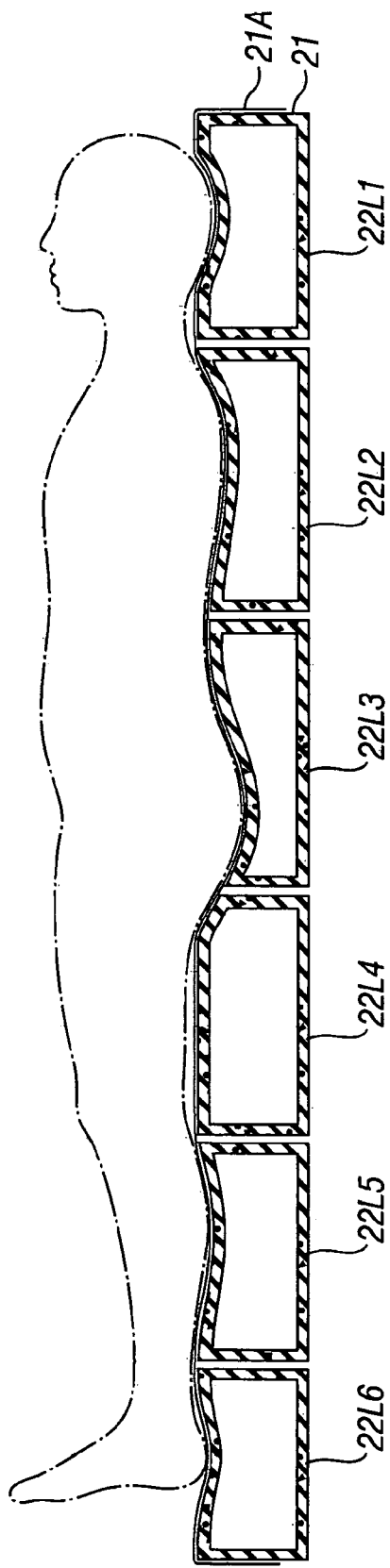

ADAPTIVE CUSHION METHOD AND APPARATUS FOR MINIMIZING FORCE CONCENTRATIONS ON A HUMAN BODY

CROSS REFERENCE TO RELATED APPLICATION

This application claims priority to U.S. patent application Ser. No. 12/075,937 filed Mar. 15, 2008 by applicant Geoffrey Taylor and entitled ADAPTIVE CUSHION METHOD AND APPARATUS FOR MINIMIZING FORCE CONCENTRATIONS ON A HUMAN BODY, the complete disclosure of which is hereby incorporated herein by reference.

BACKGROUND OF THE INVENTION

A. Field of the Invention

The present invention relates to methods, articles and apparatus for comfortably supporting a seated or recumbent human body. More particularly, the invention relates to a method and apparatus for minimizing concentration of forces on supported body parts using an adaptive cushion having a matrix of air bladder cells which are dynamically pressurized in response to measurements of body forces exerted on sensors overlying the cells.

B. Description of Background Art

Whenever a human body is supported by an object such as a chair or bed, normal and shear forces produced in reaction to the weight of the individual are transmitted from the supporting surface through the skin, adipose tissues, muscles, etc. to the skeleton. The forces exerted on body parts by support surfaces, which are equal and opposite to body weight forces, can in some cases cause damage to tissues. Forces on body parts can compress internal blood vessels and occlude nutrients from the tissue, the product of the magnitude and duration of these forces determining whether tissue damage or morbidity will occur. High pressure alone is generally not sufficient to deleteriously affect tissue. Deep-sea divers for example, are subjected to high, but evenly distributed normal forces and do not suffer from tissue damage. If, however, there is a sufficiently large external pressure gradient on a body part, resulting from, for example, a low-pressure area adjacent to a high-pressure area, internal body fluids can migrate to the area of lower pressure. Tangential or shear forces exerted externally on a body part can also collapse internal capillaries and blood vessels by distorting them along their longitudinal axes. It is therefore extremely important to know both the surface force gradient (pressure gradient) and the externally applied shear force exerted on tissue, because it is the combination of these factors that leads to tissue strain and subsequent tissue death. Thus, even relatively small external shear and normal forces, which may be independent of one another, can combine to produce damagingly large shear stresses on internal tissue. The areas of the human body which are most at risk of developing tissue damage such as a pressure sore are: heel, ischial tuberosities, greater trochanter, occiput and sacrum.

There are available a variety of pressure/force sensors, shear sensors and sensor arrays which are useable for measuring normal and shear forces exerted on human tissues. For example, the present inventor's U.S. Pat. No. 5,751,973, Nov. 5, 1996, Multi-Directional Piezoresistive Shear And Normal Force Sensors For Hospital Mattresses And Seat Cushions discloses thin, planar sensors for measuring reaction forces exerted by mattresses or chair pads on the body of a recumbent or seated patient. One embodiment of the invention disclosed in the specification of the '973 patent includes a sensor comprised of a two-dimensional array of isolated sensor element pads, each consisting of a thin, flat layer formed of a non-conductive elastomeric polymer matrix filled with electrically conductive particles.' A matrix of upper and lower conductive elements in electrical contact with upper and lower sides of each sensor pad enables separate measurements to be made of the electrical resistance of each pad. Pressure exerted on each pad, e.g., in response to a normal force exerted on the sensor matrix by a person's body, reduces the thickness of the sensor pad, and therefore its electrical resistance by a bulk or volume piezoresistive effect.

The present inventor also disclosed a novel method and apparatus for measuring pressures exerted on human feet or horses' hooves in U.S. Pat. No. 6,216,545, Apr. 17, 2001, Piezoresistive Foot Pressure Measurement. The novel apparatus disclosed in the "545 patent includes a rectangular array of piezoresistive force sensor elements encapsulated in a thin, flexible polymer package. Each sensor element includes a polymer fabric mesh impregnated with conductive particles suspended in an elastomeric matrix such as silicone rubber. The piezoresistive mesh layer is sandwiched between an array of row and column conductor strip laminations, preferably made of a nylon mesh impregnated with printed metallic paths. Each region of piezoresistive material sandwiched between a row conductor and column conductor comprises an individually addressable normal force or pressure sensor in a rectangular array of sensors, the resistance of which varies inversely in a pre-determined way as a function of pressure exerted on the sensors, and thus enabling the force or pressure. distribution exerted by an object contacting the array to be mapped.

In U.S. Pat. No. 6,543,299, Apr. 8, 2003, Pressure Measurement Sensor With Piezoresistive Thread Lattice, the present inventor disclosed a transducer sensor array for measuring forces or pressures exerted on a surface, the array including a fabric-like, two-dimensional lattice of individual force or pressure sensor transducer elements comprising intersecting regions of pairs of elongated, flexible threads, each consisting of a central electrically conductive wire core covered by a layer of piezoresistive material which has an electrical resistivity that varies inversely with pressure exerted on the material.

In U.S. Pat. No. 7,201,063, Apr. 10, 2007, Normal Force Gradient/Shear Force Sensors And Method Of Measuring Internal Biological Tissue Stress, the present inventor disclosed a normal force gradient/shear force sensor device and measurement method for measuring internal stresses in tissues of a person supported by a chair or bed. The device includes a planar matrix array of peripheral normal force sensors radially spaced from central shear force sensors, each including an electrically conductive disk located within a circular opening bordered by circumferentially spaced apart electrodes. The disk and electrodes are located between upper and lower cover sheets made of a stretchable material such as polyurethane, one cover sheet being adhered to the disk and the other sheet being adhered to a support sheet for the electrodes. Motion between the cover sheets in response to shear forces exerted on the array causes the disk to press more or less tightly against the electrodes, thus varying electrical conductance between the disk and electrodes proportionally to the magnitude and direction of the shear force. Each normal force sensor includes an electrically conductive film pressed between row and column conductors. Measurements of conductance values of pairs of sensor, which vary proportionally to normal forces exerted on the sensor, are used to calculate a gradient vector of normal forces exerted by a body part on the sensor array, which is combined with the shear force vectors in an algorithm to calculate internal reaction shear forces, e.g., on flesh near a bony prominence.

The first group of the present inventor's patents identified above disclosed shear and normal force sensors and arrays which are useful in producing maps of normal and shear forces exerted at discrete points on a surface, such as a human body part, by an object such as the supporting surface of a chair or bed. The last of the present inventor's patents identified above provided an effective means for measuring shear forces and stresses on human tissue which is located some distance below the surface of the skin.

In U.S. Pat. No. 6,721,980, Force Optimization Surface Apparatus And Method, the present inventor and co-inventors disclosed an apparatus including a mattress which included a plurality of laterally disposed, tubular sausage-shaped air bladders, each having thereon an individual force sensor. The apparatus included a mechanism for individually inflating each of the air bladders, monitoring the pressure in each individual bladder while a person was lying on the mattress monitoring the force exerted on that particular bladder, adjusting the pressure of that individual bladder for the purpose of minimizing force exerted by that particular bladder on the person's body, and repeating the foregoing steps for each bladder cell in turn.

The method described in U.S. Pat. No. 6,721,980 of measuring force exerted by a person's body on a single individual air bladder cell while adjusting the inflation pressure in that cell may be suitable for single air bladder systems, and for those conditions in which the body of a supported patient freely conforms to the support surface. However, for the more frequently encountered cases in which portions of a patient's body are straddled between and supported by adjacent air bladder cells, the force measured on a particular bladder whose air pressure is bing adjusted may be minimal for a particular inflated pressure. But the pressure which may minimize force exerted on a particular air bladder cell will in general not be the optimum pressure for minimum total force concentrations on a person's body. This is because while the force exerted on a particular air bladder cell may be minimized, forces exerted on air bladder cells adjacent to the air bladder cell in which the pressure is being varied may be substantially increased because the load weight is shifted to the adjacent cells.

A similar limitation of the prior art methods and apparatus occurs when a portion of a patient's body is supported in a cantilevered manner from one or more adjacent air bladder cells while pressure is varied in a particular air bladder cell. Again in that case, load forces are transferred to adjacent air bladder cells. Accordingly; it would be desirable to provide a method and apparatus which accounted for all forces exerted on all air bladder cells while varying pressure in any individual cell The present invention was conceived of to provide a method and apparatus for minimizing body force concentrations on parts of a human body supported by a chair or bed cushion, which includes measuring forces exerted on body parts.

OBJECTS OF THE INVENTION

An object of the present invention is to provide an adaptive cushion method and apparatus for minimizing reaction forces exerted by a bed, chair or other such object on body parts of a person lying or seated on the object.

Another object of the invention is to provide an adaptive cushion method and apparatus which includes an overlay cushion for placement on a bed mattress or chair, the cushion including a matrix of individually pressurizable air bladder cells and an array of surface force sensor transducers which includes an individual sensor vertically aligned with each air bladder cell, and an electronic control system for receiving force sensor signals and dynamically varying inflation pressures applied to individual air bladder cells to inflate or deflate the individual cells to pressures calculated by a control system algorithm to minimize force concentrations on parts of a body supported by the cushion.

Another object of the invention is to provide stretchable surface force transducers which are conformable to protuberances of a human body.

Another object of the invention is to provide stretchable surface force sensors which have an asymmetric, diode-like current-versus-voltage transfer function.

Another object of the invention is to provide a matrix array of stretchable surface force sensor transducers which have a non-bilateral current-versus-voltage transfer functions, thus minimizing cross-talk ambiguities occurring during X-Y addressing of individual sensors to map forces exerted on the array.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, I do not intend that the scope of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly stated, the present invention comprehends a method and apparatus for minimizing high concentrations of reaction forces exerted by a chair, bed or other such object on protruding parts of the body of a person seated or lying on the object. A body force minimization apparatus according to the present invention includes an adaptive cushion for placement on a mattress or chair, the cushion having a matrix of air bladder cells which are individually pressurizable by means of an air compressor and valves to variable pressures.

In a typical embodiment of the adaptive cushion suitable for use on bed, the air bladder cells may be arranged in a 6×2, X-Y rectangular grid, thus dividing the cushion into left and right columns, each having 6 longitudinally spaced apart zones running in the long, head-to-feet direction of the bed.

The adaptive cushion apparatus according to the present invention also includes a flexible, stretchable planar array of force sensor transducers of novel construction, which is preferably positioned on the upper surface of the cushion, the array having at least one sensor in vertical alignment with each air bladder cell of the cushion.

The sensor array according to the present invention includes stretchable fabric row and column conductors which have sandwiched between inner facing conductive surfaces thereof a stretchable fabric sheet coated with a piezoresistive material. Thus constructed, the planar sensor array is elastically deformable in response to forces exerted on the array by the weight of a human body supported on the upper surface of the sensor array overlying the air bladder cells. Preferably, the sensor array placed on the upper surfaces of the air bladder cells and maintained in that position by a form-fitting, waterproof, contour sheet. The fabric matrices for both row and column conductors, as well as the central piezoresistive layer, are all made of a material which is elastically deformable in any direction within the plane of the material. In a preferred embodiment, the fabric matrices or the row conductor sheet and column conductor sheet are plated with a copper base coat and nickle cover coat. The central piezoresistive sheet consists of a synthetic fabric matrix coated with piezoresistive coating. The sensor array also has an upper cover sheet which is made of a fabric such as Lycra which has a two-way stretch characteristic, i.e., is elastically stretchable in orthogonal directions.

An adaptive cushion apparatus according to the present invention includes an electro-pneumatic controller which is effective in alternately pressurizing and venting individual air bladder cells to control pressures, in respect to forces exerted by a human body on individual sensors aligned with the air bladder cells. The electro-pneumatic controller includes an electronic control system for applying a voltage or current individually to each force sensor and measuring the resultant current or voltage to thereby determine electrical resistance of the sensor, which is inversely proportional to the force or pressure exerted on the sensor, by for example, a person seated or lying on the cushion covered by the sensor array.

The electronic control system also includes a computer which receives as inputs electrical signals from individual sensors representative of their resistance, and hence forces or pressures exerted on the upper surface of each sensor.

The body force minimization apparatus according to the present invention also includes a pneumatic system which has a source of pressurized air, such as a compressor, for inputting pressurized air through a manifold and individually controllable inlet selector valves to each individual air bladder cell. The apparatus also includes an air pressure transducer for monitoring the air pressure within a selected cell, and outputting to the computer an electrical signal representative of the measured pressure.

Each air bladder cell inlet valve is electrically operable and has a first, open position in which air from an outlet port of the manifold is conducted to a selected air bladder cell to inflate it to a desired set pressure, and a second, closed position effective in maintaining a desired set pressure within the cell.

The pneumatic system also includes a vent valve coupled to the inlet port of the manifold. With the vent valve and a selected air bladder cell value in a second, open position, pressurized air from a selected air bladder cell is vented to the atmosphere through a exhaust port of the vent valve to reduce the pressure in the individual air bladder cell to a lower controllable value. Each valve is electrically connected to an output control port of the computer; and operably controllable by signals on the output control port.

The present invention also includes a method for electronically controlling the body force minimization apparatus. The method includes an algorithm implemented in the control system computer. That algorithm receives as inputs force measurements from individual air bladder cells, and outputs command signals which individually adjust the air pressure in each air bladder cell to values which are effective in minimizing force concentrations on body parts supported by the cushion.

According to the algorithm, each of the air bladder cells is inflated to predetermined upper set pressures, which may be the same or different for different cells, prior to a person's lying or sitting on the cushion. Next, a person is positioned on the cushion, while forces exerted by the person's body on each sensor are initially monitored by computer controlled measurement of the electrical resistance of each force sensor. A first, "zone-one" air bladder cell is then deflated under computer control to a predetermined lower set pressure. Although zone-one may correspond to any individual air bladder cell, such as the upper left-hand corner cell value in a 6-row by 2-column of air cells for use on a bed, a preferred mode of operation is to choose as zone-one the cell on which the highest body force was measured during the initial monitoring process.

During the step of deflating the first, zone-one air bladder cell, which is done in a slowly varying, ramped fashion, the forces exerted on each of the cells including the zone-one cell are measured, and the sum and optionally the average of those forces calculated by the computer. At the end of the downwardly ramped deflation step, the air pressure corresponding to the lowest sum and average of all force sensor readings is noted. The zone-one cell is then re-inflated to that pressure corresponding to the lowest sum and average force sensor readings, to complete the cycle for zone-one.

The pressure-ramping cycle described above for the first zone, i.e., zone-one, is repeated in turn for each remaining zone of the air bladder cell cushion. Preferably, the sequence of zone deflation, re-inflation pressure-ramping cycles corresponds to successively smaller force concentrations. In other words, zone-one is chosen as the zone at which the highest surface body force was measured, zone-two would correspond to that zone having the second highest body force measurement, etc.

After the pressure-ramping cycle has been completed for each of the zones of the adaptive cushion, those steps are repeated for all of the zones, but using a reduced range of pressure, i.e., lower upper set pressures and higher lower set pressures. The sequence is then repeated again until the successively smaller adjustments in force measurements fall below a predetermined threshold level, at which time the cyclical operation of the system reverts to a passive state.

In the passive state, the computer monitors each of the force sensor outputs. Restoration of the control system to active cyclical operation is initiated by a significant change of any force measurement above a predetermined threshold in response, for example, to patient movements.

BRIEF DESCRIPTION OF THE DRAWINGS

FIG. 2A is a fragmentary upper perspective view of the apparatus of FIG. 1, showing a sensor array jacket of the apparatus removed from a mattress overlay cushion of the apparatus to thereby reveal individual air bladder cells of the mattress.

FIG. 2B is a fragmentary view of the mattress overlay of FIG. 2A, showing an individual air cell thereof.

FIG. 3 is a diagrammatic side elevation view of the apparatus of FIGS. 1 and 2, showing certain bladder cells thereof deflated to reduce support forces exerted on parts of a human body supported by the mattress overlay.

FIG. 4 is a vertical sectional view of the mattress of FIG. 2, taken in the direction of line 4-4.

DESCRIPTION OF THE PREFERRED EMBODIMENTS

FIGS. 1-11 illustrate various aspects of a method and apparatus for minimizing body force concentrations on a human body using an adaptive cushion according to the present invention. The example embodiment of the invention depicted in FIGS. 1 and 3, includes an adaptive cushion which is of an appropriate size and shape for use on a standard single or hospital bed. However, as will be clear from the ensuing description of that example embodiment, the size and shape of the adaptive cushion can be varied to suit different applications, such as for use on a fixed chair or wheel chair.

Figure 1:
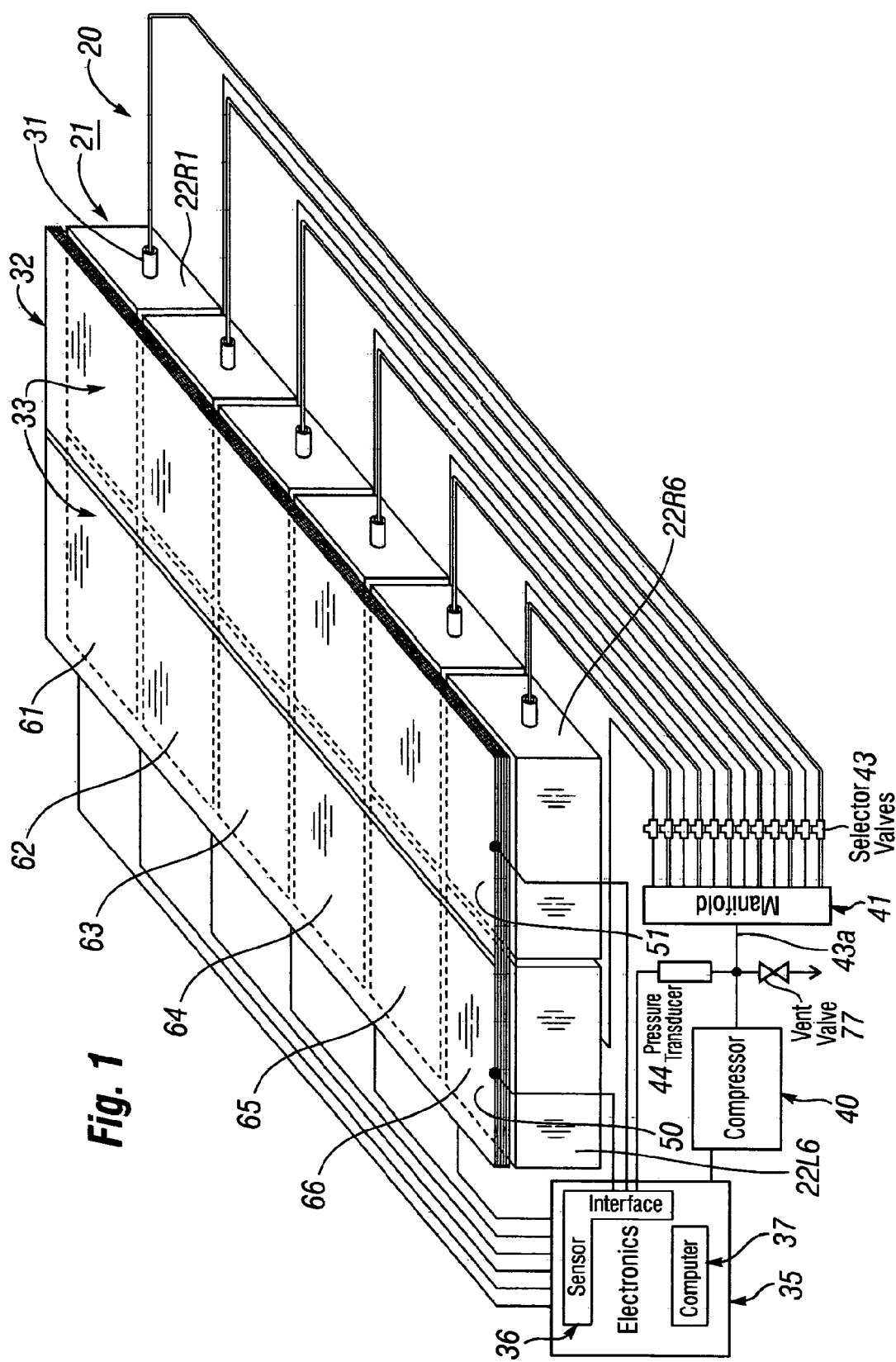
FIG. 1 is a partly diagrammatic perspective view of a body support cushion apparatus with adaptive body force concentration minimization according to the present intention.

Referring first to FIGS. 1 and 2, an adaptive cushion apparatus 20 for minimum body force concentrations on a body of a person lying on a bed may be seen to include a longitudinally elongated, rectangular cushion overlay 21. Cushion 21 has an appropriate size and shape to fit conformally on top of a standard size hospital bed. Thus, an example embodiment of cushion 21 had a laterally elongated, rectangular shape with a length of about 6 feet, a width of about 3 feet, and a thickness of about 4 inches.

The six panels of each air bladder cell 23 are sealingly joined at edges thereof to form a hermetically sealed body which has a hollow interior space 22A.

As shown in FIG. 2, mattress overlay cushion 21 is constructed as a rectangular, two-column by six-row array of 12 individual inflatable air bladder cells 22. Each air bladder cell 22 has a laterally elongated, rectangular shape, having a length of about 18 inches, a depth of about 17 inches, and a thickness of about 4 inches. As shown in FIGS. 1 and 2, bladders 22 are arranged in left and right columns, each having 6 longitudinally spaced apart, laterally disposed, laterally elongated bladders. As shown in FIGS. 2 and 4, each air bladder cell has a flat base panel 23, left and right end panels 24, 25, head and toe or front and rear panels 26, 27, and an upper panel 28. The bladders 22 are preferably made of a thin sheet of a flexible, preferably elastomeric material such as neoprene rubber or polyurethane, having a thickness of about 0.014 inch. Optionally, each air bladder cell may be fabricated from a tubular preform in which each end panel is sealingly joined to opposite transverse ends of the tubular preform. In either embodiment, adjacent panels of an individual air bladder cell are sealingly joined by a suitable method such as ultrasonic bonding, RF-welding or adhesive bonding.

The number, size, shape, relative positioning and spacing of air bladder cells 22 of mattress cushion overly 21 are not believed to be critical. However, it is believed preferable to arrange mattress overlay 21 into symmetrically-shaped left and right columns each having at least five and preferably six longitudinal zones corresponding to major curvature of a longitudinally disposed medial section of a typical human body. Thus, as shown in FIGS. 1, 2A and 3, mattress overlay cushion 21 has a left-hand column of six air bladder cells 22L1-22L6, and a right-hand column of six cells 21R1-21R6.

Figure 6:
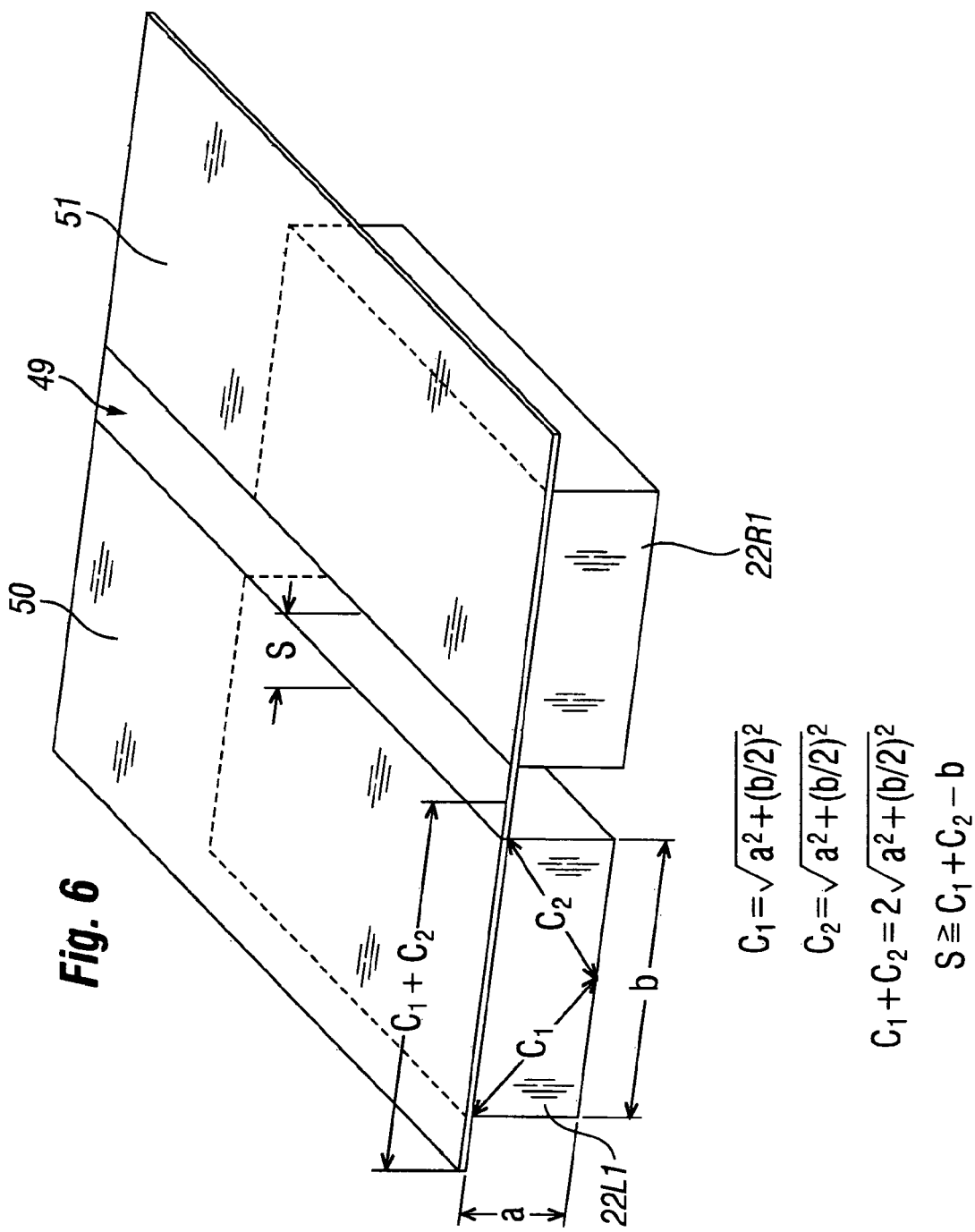
FIG. 6 is a diagrammatic view showing a preferred relationship between the dimensions of adjacent air bladder cells and the width of an insulating strip between conductors of sensors on the cells.

As shown in FIGS. 4 and 6, the bladders are stacked closely together in both front and rear and side by side directions, with minimum longitudinal and lateral spacings 29, 30, respectively, that are preferably vanishingly small so that adjacent bladder cells physically contact each other.

As indicated in FIGS. 1 and 2, each bladder cell 22 is provided with a tubular air inlet port 31 which protrudes through a side wall, e.g., a left or right side wall 24 or 25, and communicates with a hollow interior space 22A within the bladder. Air admitted into or exhausted from hollow interior space 22A through port 31 of an air bladder cell 22 enables the cell to be inflated or deflated to a selected pressure.

Although the shape of each air bladder cell 22 of-cushion 21 shown in FIGS. 1 and 2 is that of a rectangular block, or parallelepiped, the air bladder cells may optionally have different shapes, such as convex hemispheres protruding upwards from the base of the cushion. Also, the array of air bladder cells 22 of cushion 21 may be parts of a unitary structure with a common base panel 23 which has individual rectangular-block shaped, hemispherical or hollow inflatable bodies of other shapes protruding upwardly from the common unitary base panel.

Whether individual air bladder cells 22 are separate bodies or upper inflatable shell-like portions protruding upwardly from a common base, air inlet/exhaust port tubes 31 of each air bladder cell 22, or selected air bladder cells 22, may be located in the base panel 23 of the cell and protrude downwardly from the cell, rather than being located in a side wall and protruding outwardly, as shown in FIGS. 1 and 2.

Figure 5:
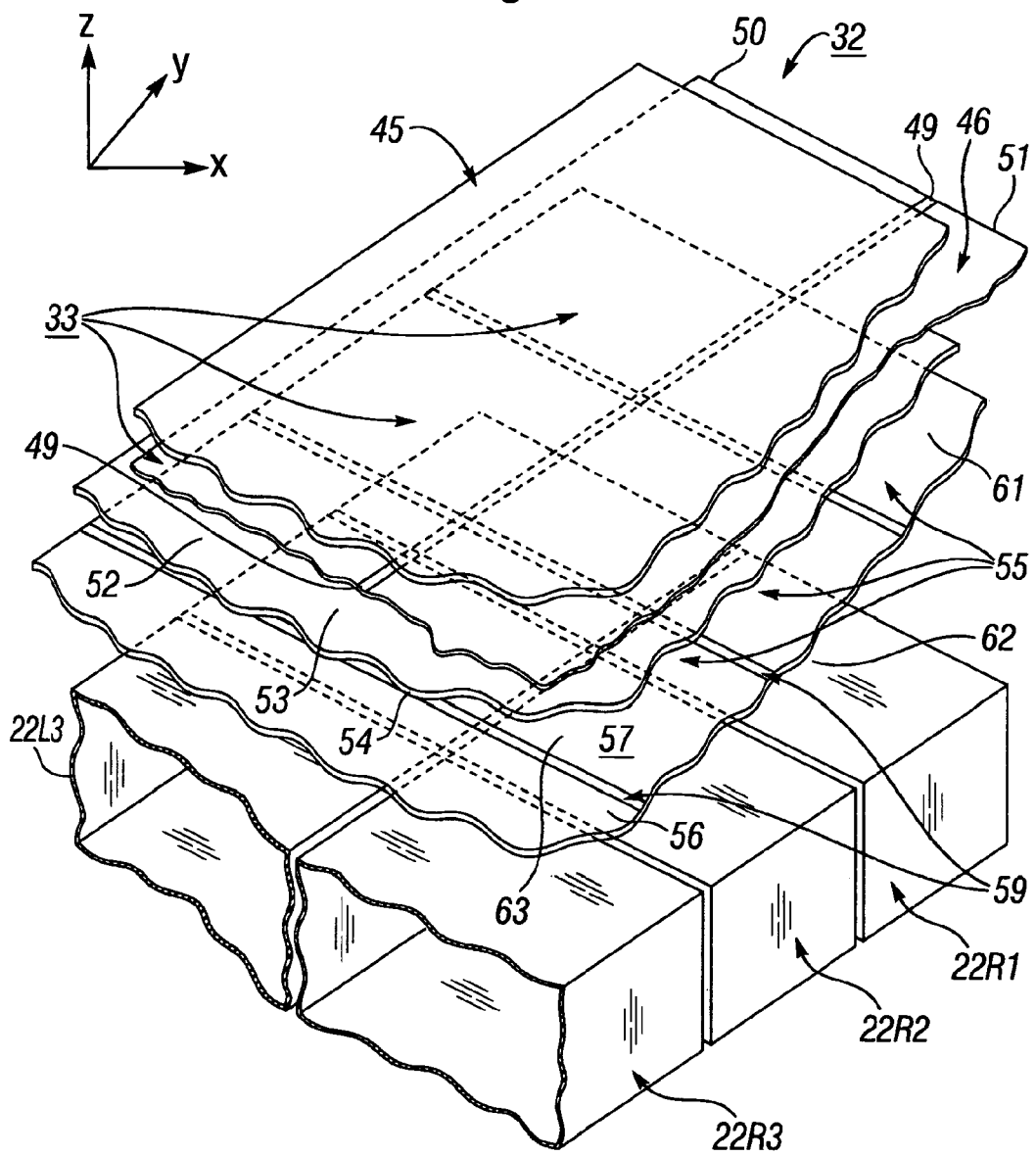
FIG. 5 is a fragmentary exploded perspective view of the mattress of FIG. 1, showing elements of a force sensor arrangement thereof.

As shown in FIGS. 1, 2 and 5, body force minimization apparatus 20 includes a force sensor array 32 which has a matrix of individual force sensors 33, with at least one sensor positioned on the upper surface 34 of each air bladder cell 22. As will be explained in detail below, each force sensor 33 is a force sensitive transducer which has an electrical resistance that varies inversely with the magnitude of a normal, i.e., perpendicular force exerted on the sensor by an object such as the body of a person supported by overlay cushion 21. In a preferred embodiment, force sensor array 32 is maintained in position on the upper surfaces of air bladder cells 22 by a water-proof, form-fitting contour fabric sheet 21A which fits tightly and removably over cushion 21, as shown in FIG. 3.

Referring to FIG. 1, it may be seen that body force minimization apparatus 20 includes an electronic control module 35. As will be explained in detail below, electronic control module 35 includes sensor interface circuitry 36 for electrical interconnection to sensors 33. Electronic control module 35 also includes a computer 37 which is interconnected with sensor interface circuitry 36. Computer 37 is programmed to receive input signals from sensor interface circuitry 36, measure the resistance of individual sensors 33 and calculate therefrom the magnitude of forces exerted on each sensor, make calculations based on the force measurements, and issue command signals to control the pressure in individual air bladder cells 22 which are calculated to minimize force concentrations on the cells.

In a preferred embodiment of apparatus 20, measurement of the resistance of each sensor 33 is facilitated by arranging the sensors into a matrix array of rows and columns. With this arrangement, individual resistances of a 6×2 array 32 of sensors 33 may be measured using 6 row interface conductors 35 and a 2 column interface conductors 39, as shown in FIG. 1.

To avoid cross talk between measurements of individual sensors 33, the aforementioned row-column addressing arrangement requires that each sensor have a non-bilateral, asymmetric current versus voltage characteristics, e.g., a diode-like impedance characteristic. As will be described in detail below, the present invention includes a novel sensor having the required diode-like characteristic. Alternatively, using force sensors 33 which do not have a diode-like characteristic, the force sensor array 32 can be partitioned into 12 separate rectangular sensors 33 each electrically isolated from one another, with a separate pair of interface conductors connected to upper and lower electrodes of each sensor.

As shown in FIG. 1, body force minimization apparatus 20 includes an air pump or compressor 40 for providing pressurized air to the input port 42 of a selector valve manifold 41. Selector valve manifold 41 has 12 outlet ports 43A, each connected through a valve 43 to a separate air bladder cell inlet port 31. As will be explained in detail below, the compressor 40, selector valve manifold 41 and valves 43 are operably interconnected to computer 37 and an air pressure transducer 44. Pressure transducer 44 outputs an electrical signal proportional to pressure, which is input to computer 31. This arrangement enables the inflation pressure of each air bladder cell 22 to be individually measured and varied under control of the computer 37.

FIGS. 2, 4 and 5 illustrate details of the construction of force sensor array 32. As shown in those figures, sensor array 32 includes an upper cover sheet 45 made of a thin flexible, elastically stretchable material. In an example embodiment of sensor array 32 fabricated by the present inventor, cover sheet 45 was made of "two-way stretch" Lycra-like material which had a thickness of about 0.010 inch and a thread count of about 88 threads per inch. That material had the trade name Millglass Platinum, Style No. 247579, obtained from the Milliken & Company, P.O. Box 1926, Spartanburg, S.C. 29304.

Referring to FIG. 5, sensor array 32 includes an upper, column conductor sheet 46 which is fixed to lower surface 47 of upper flexible cover sheet 45, by flexible adhesive strips 47 made of 3M transfer tape 950, or a flexible adhesive such as Lepage's latex contact adhesive. Column conductor sheet 46 is made of a woven fabric matrix sheet composed of 92% nylon and 8% Dorlastan fibers; which give the sheet a flexible, two-way stretch elasticity. The fabric matrix sheet of conductor sheet 46 is electroless plated with a base coating of copper, followed by an outer coating of nickle. The metallic coatings completely impregnate the surfaces of fibers adjacent to interstices of the mesh fabric, as well as the upper and lower surfaces 47 48 of the conductor sheet 46, thus forming electrically conductive paths between the upper and lower surfaces 47 and 48. The present inventor has found that a suitable conductive fabric for conductor sheet is a Woven Silver brand, Catalog #A251 available from Lessemb Company, 809 Madison Avenue, Albany, N.Y. 12208, USA.

In an example embodiment of sensor array 32, upper conductive sheet 46 was fabricated from the Woven Silver, Catalog #A151 material described above. The surface resistivity of upper and lower surfaces 47, 48 of that material was about 1 ohm per square or less, and the inter-layer resistance between upper and lower surfaces 47, 48 was about 50 ohms per square.

In a preferred embodiment of sensor array 32 according to the present invention, individual conductive pads, or rows or columns of conductors; are formed by etching metal-free channels vertically through conductor sheet 46, from the top of upper conductive surface 47, all the way to the bottom of lower conductive surface 48. Thus, as shown in FIG. 5, narrow longitudinally disposed straight channels 49 are etched through upper column conductor sheet 46. This construction results in the formation of two adjacent, relatively wide, longitudinally elongated left and right planar column electrodes 50, 51. The adjacent left and right column electrodes are separated by a relatively thin channel 49, thus electrically isolating the adjacent column electrodes from each other.

According to the present invention, insulating channels 49 are etched through upper conductor sheet 46 to form column electrodes 50 and 51 by the following novel process.

First, to prevent capillary wicking and resultant wetting of a subsequently applied etchant solution to fabric conductor sheet 46, the sheet is, pre-processed by treating it with a hydrophobic substance such as PTFE. The treatment is preferably made by spraying the conductor fabric sheet 46 with an aerosol containing a hydrophobic material such as PTFE. A suitable aerosol spray is marketed under the trade name Scotch Guard by the 3M Company, St. Paul, Minn. Preferably, areas of fabric conductor sheet 46 which are to have insulating channels 49 formed therein are masked from the hydrophobic treatment by adhering strips of masking tape which have the shape of the channels to the sheet before applying the hydrophobic material to the sheet.

Following the pre-processing of conductor sheet 46 to make it hydrophobic, sheets of masking tape are adhered tightly to both upper and lower surfaces 47, 48 of the conductor sheet, using a roller or press to insure that there are no voids between the masking tape and surfaces, which could allow etchant solution to contact the conductive surfaces. Next, strips of masking tape having the shape of insulating channels 49 are removed from the conductor sheet. Optionally, the strips of masking tape to be removed are preformed by die-cutting partially through larger sheets of masking tape.

After strips of masking tape corresponding to channels 49 have been stripped from conductor sheet 46, the conductive metal coatings of the fabric sheet aligned with the channels is chemically etched away. A preferred method of performing the chemical etching uses a concentrated solution of 10 mg ammonium phosphate in 30 ml of water. The ammonium phosphate solution is mixed with methyl cellulose solid powder, at a concentration of 10 percent methyl cellulose-powder until a gel consistency is obtained. The etchant gel thus formed is then rollered onto the areas of upper and lower surfaces 47, 48 of conductor sheet 46, over channels 49. The etchant gel is allowed to reside on channels 49 for approximately 1 hour, at room temperature, during which time the nickel and copper plating of the fabric matrix of conductor sheet 46, in vertical alignment with channels 49, is completely removed, thus making the channels electrically insulating. This process separates the conductor sheet into left and right column electrodes 50, 51, respectively.

The etching process which forms insulating channel 49 is completed by rinsing the etchant gel from upper and lower surfaces 47, 48 of conductor sheet 46, followed by removal of the masking tape from the upper and lower surfaces.

Referring still to FIG. 5, it may be seen that sensor array 32 includes a thin piezoresistive sheet 52 which has on an upper surface 53, that is in intimate contact with lower surfaces of left and right column electrodes 50, 51. Piezoresistive sheet 52 also has a lower surface 54 which is in intimate electrical contact with the upper surfaces of row electrodes 55 on a lower row conductor sheet 56. Lower, row conductor sheet 56 has a construction exactly similar to that of upper, column conductor sheet 46. Thus, lower row conductor sheet 56 has upper and lower conductive surfaces 57, 58, and narrow, laterally disposed insulating channels 59 which are positioned between and define row electrodes. 61, 62, 63, 64, 65, 66.

The function of piezoresistive sheet 52 of sensor array 32 is to form a conductive path between column and row electrodes, e.g., left-hand column electrode 50 and rear row electrode 61, the resistance of which path varies in a predetermined fashion as a function of normal force exerted on the sensor array.

In example embodiments of sensor array 32, piezoresistive sheet 52 was fabricated by coating a stretchy, thin Lycra-like fabric sheet with a piezoresistive material. A suitable fabric sheet, which forms a matrix for supporting the piezoresistive material, was a fabric known by the trade name Platinum, Milliken, Style #247579, obtained from the manufacturer, Milliken & Company, Spartenburg, S.C., USA. That fabric had a fiber content of 69 percent nylon and 31 percent Spandex, a thread count of about 88 threads per inch, and as thickness of 0.010 inch. The piezoresistive material used to coat the fabric matrix is made as follows:

A solution of graphite, carbon powder, nickel powder and acrylic binder are mixed in proportions as required to obtain the desired resistance and piezoresistive properties. Silver coated nickel flake is used to achieve force response in the low force range of 0 to 1 psi, graphite is used for the mid range of 1 to 5 psi and Charcoal Lamp Black is used for high force range of 5 to 1000 psi. Following is a description of the substances which are constituents of the piezoresistive material:

Silver Coated Nickel Flake:
Platelets approximately one micron thick and 5 microns in diameter.
Screen Analysis (−325 Mesh) 95%.
Apparent Density 2.8.
Microtrac d50/microns 12-17.
Available from: Novamet Specialty Products Corporation,
681 Lawlins Road, Wyckoff, N.J. 07481
Graphite Power:
Synthetic graphite, AC-4722T
Available from: Anachemia Science
4-214 DeBaets Street
Winnipeg, MB R2J 3W6
Charcoal Lamp Black Powder:
Anachemia Part number AC-2155.
Available from: Anachemia Science
4-214 DeBaets Street
Winnipeg, MB R2J 3W6
Acrylic Binder:
Staticide Acrylic High Performance Floor Finish
P/N 4000-1 Ph 8.4 to 9.0.
Available from: Static Specialties Co. Ltd.
1371-4 Church Street
Bohemia, N.Y. 11716
Following are examples of mixtures used to make piezoresistive materials having different sensitivities:
Example I for forces in the range of 0 to 30 psi:
200 ml of acrylic binder
10 ml of nickel flake powder
10 ml of graphite powder
20 ml of carbon black
Example II for forces in the range of 0-100 psi
200 ml of acrylic binder
5 ml of nickel flake powder
5 ml of graphite powder
30 ml of carbon black
Example III for forces in the range of 0-1000 psi
200 ml of acrylic binder
1 ml of nickel flake powder
1 ml of graphite powder
40 ml of carbon black The fabric matrix for piezoresistive sheet 52 is submerged in the piezoresistive coating mixture. Excess material is rolled off and the sheet is hung and allowed to air dry.

FIG. 6 illustrates calculation of a minimum spacing S between adjacent air bladder cells 22, and a minimum width of non-conductive strip 49 between adjacent conductors of sensor array 32.

Referring to FIG. 6, as a patient sinks into a deflating bladder 22, the upper force sensor layer 33 is drawn down and away from the bladder over which it was initially positioned. If the non-conductive strip 49 is too narrow, there is a possibility that the conductive portion will overlay the deflating bladder and, thus register forces that are not representative of the force over the bladder in which it was originally positioned. It is therefore necessary to make the non-conductive strip 49 wide enough to prevent this from happening. If we assume a simple situation wherein an air bladder cell is deflated until the center of the cell, then the force sensing layer is drawn down a distance equal to the diagonals (C1 and C2) as shown in FIG. 6, the width S of non-conductive strip 49 should be made equal to or greater than (C1+C2−the width of the bladder) to prevent forces being misread as coming from a neighboring cell.

Figure 7:
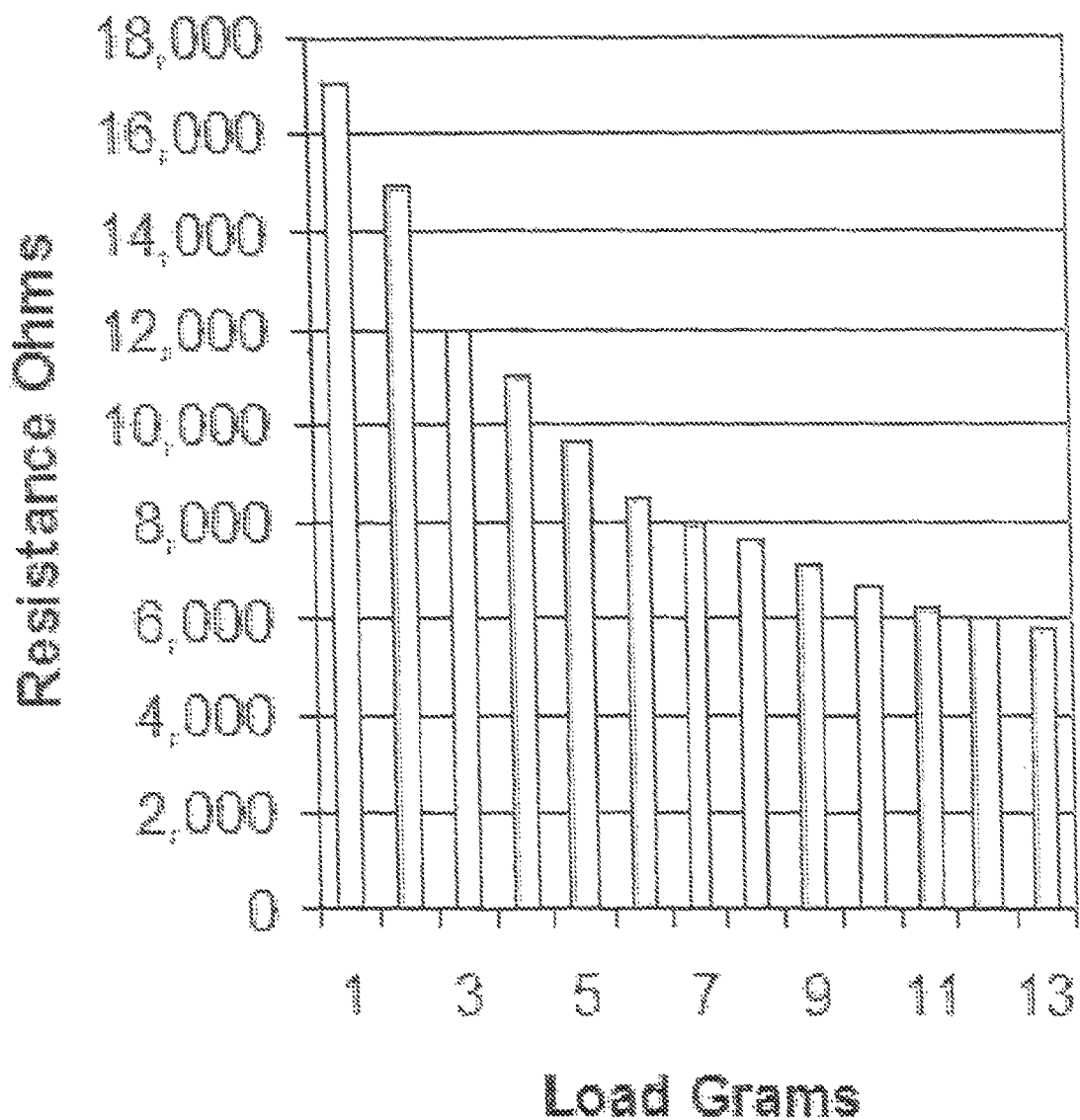
FIG. 7 is an electrical resistance-vs.-normal force diagram for the sensors of FIG. 5.

FIG. 7 illustrates the electrical resistance of a one-inch square force sensor 33 using a piezoresistive sheet 52 having the formulation listed for example I above, and fabricated as described above, as a function of normal force or pressure exerted on the upper surface of cover sheet 45 of sensor array 32. As shown in FIG. 7, the resistance varies inversely as a function of normal force.

As shown in FIGS. 1 and 5, left and right column electrodes 50 and 51, in vertical alignment with row electrodes 61, 62, 63, 63, 65, 66, of 12 form with piezoresistive layer sheet 52 between the column and row electrodes a 2×6 rectangular matrix array of 12 force sensors 33.

Optionally, the upper and lower electrodes for each sensor 33 could be segmented into electrically isolated rectangular pads by etching channels 49, 59 through both upper conductive sheet 46 and lower conductive sheet 56. This arrangement would require a separate pair of lead-out conductors for each of the 12 sensors, i.e., a total of 24 leads.

Preferably, as shown in FIGS. 1 and 5, sensor array is arranged into rows and columns, thus requiring only 8 lead-out conductors. However, as shown in FIG. 10A, if matrix addressing of sensor array 32 is used to measure the resistance of individual sensors 33 to thereby determine normal forces exerted on the sensors, there is a substantial cross-talk between the resistance on an addressed sensor 33 and non-selected sensors because of parallel current paths to non-addressed sensors. To overcome this cross-talk problem, the present inventor has developed a method for modifying sensors 33 to give them a diode-like characteristic. As may be confirmed by referring to FIG. 10B, the cross-talk between sensors 33 which have a non-bilateral, polarity-sensitive transfer function, mitigates the cross-talk problem present in the matrix of symmetrically conductive sensors 33 shown in FIG. 10A.

Sensors 33 are modified to have a diode-like characteristic by modifying the preparation of piezoresistive layer sheet 52, as follows: First, a piezoresistive layer sheet 52 is prepared by the process described above. Then, either the upper surface 69 or the lower surface 70 of the piezoresistive coating 67 of Piezoresistive sheet 52 is modified to form thereon a P-N, semiconductor-type junction.

Modification of piezoresistive coating 67 to form a P-N junction is performed by first preparing a slurry which has the composition of one of the three example mixtures described above, but modified by the addition of 5 ml each of copper oxide (CuO) in the form of a fine powder of 50-micron size particles, and 5 ml of cuprous oxide ($Cu_2O$) in the form of a fine powder of 50-micron size particles and thoroughly stir-mixing the foregoing ingredients. The resultant solution is then reduced using about 30 mg of solution of sodium borohydride, also known as sodium tetrahydroborate ($NaBH_4$) or ammonium phosphate, to form a solution having a pH of about 5.5. The solution is then coated onto the upper surface 69 or lower surface 70 of piezoresistive coating 68 on piezoresistive sheet 52. This coating process is performed using a roller coating process which results in about 0.5 ml of solution per square centimeters being applied. The surface coating is then allowed to air-dry at room temperature and a relative humidity of less than 20%, for 4 hours. After the coated surface has dried, it functions as a P-type semiconductor, while the uncoated side of coating 68 functions as an N-type semiconductor of P-N junction diode.

Figure 8:
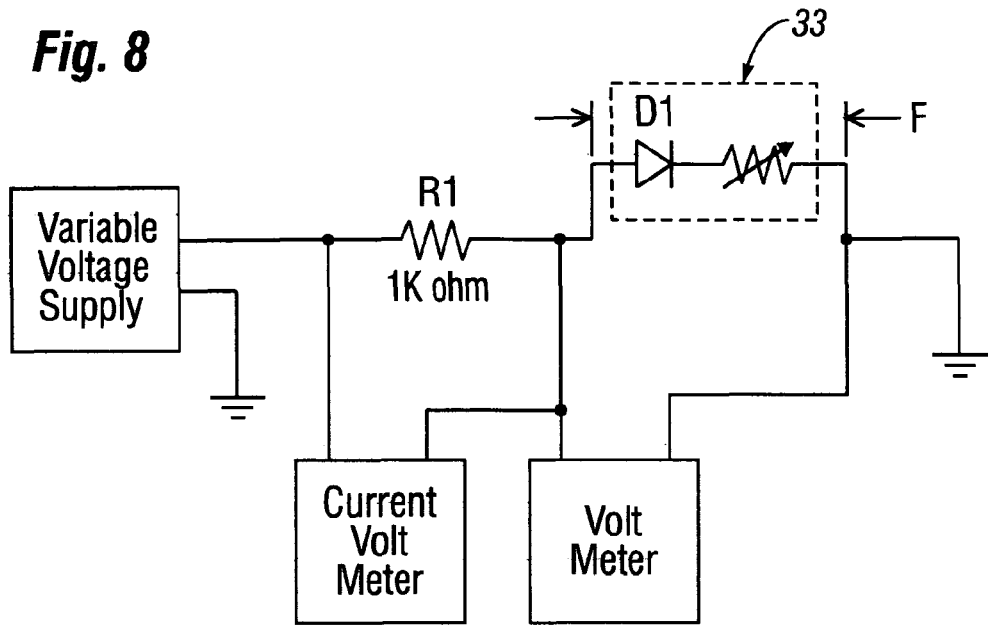
FIG. 8 is a partly schematic view of a preferred modification of sensor elements of the array of FIG. 1, which includes a diode junction.
Figure 9:
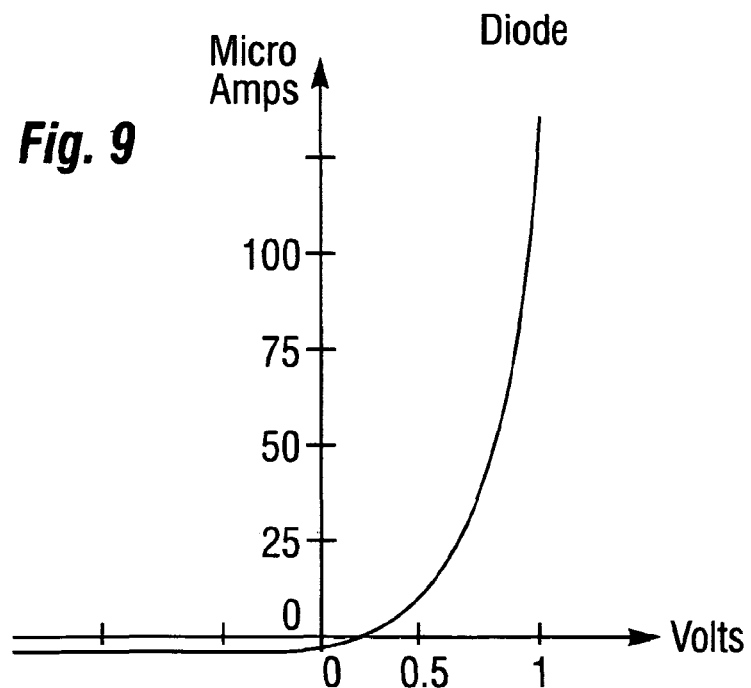
FIG. 9 is a current-vs-voltage (I-V) diagram for the sensor elements of FIG. 8.

FIG. 8 illustrates a sensor 33 which has been prepared as described above to give the sensor a diode-like characteristic, and a circuit for obtaining the I-V (current versus voltage) transfer function of the sensor. FIG. 9 shows a typical I-V curve for sensor 33 of FIG. 8.

As stated above, the advantage of modifying sensors 33 by adding a semi-conductive layer that acts like a diode is that it reduces cross talk between sensors. As is shown in FIG. 10A, this cross-talk occurs because of the so-called "completing the square" phenomenon, in which three connections are made in a square matrix array of three non-addressed resistors that form the three corners of a square. Thus, any two connections in a vertical column and a third one in the same row function as either connection in an X-Y array of conductors. The resistor at the fourth corner of the square shows up as a phantom in parallel with an addressed resistor because the current can travel backwards through that resistor, and forward through the other resistors. Care and additional expense must be taken in the electronics to eliminate the contribution of this phantom. For example, if, as is shown in FIG. 10A, a potential V is applied between row and column conductors $X_1Y_1$, to thereby determine the resistance of piezoresistive sensor resistance $R_{11}$, reverse current flow through "phantom" resistor $R_{22}$ would cause the sum of resistances $R_{12}+R_{22}+R_{22}$ to shunt $R_{11}$, resulting in the parallel current flow paths indicated by arrows in FIG. 10A, which in turn would result in the following incorrect value of resistance:

$$R_{x1}Y_1=R_{11}//(R_{12}+[R_{22}]+R_{21})_1R_{x1}Y_1=R_{11}(R_{12}+[R_{22}]+R_{21})/(R_{11}+R_{12}+[R_{22}]+R_{21})_1$$

where brackets around a resistance value indicate current flow in a counterclockwise direction through that resistor, rather than clockwise, i.e., diagonally downwards towards the left. Thus, for example, if each of the four resistances listed above had a value of 10 ohms, the measured value of $R_{11}$ would be:

$$R_{11}=10(10+10+10)/(10+10+10+10)=300/40=7.5$$
ohms, i.e., 25% below the actual value, 10 ohms, of $R_{11}$.

If the resistance values of $R_{12}$, $R_{22}$ and $R_{21}$ of the three non-addressed piezoresistive sensors 33 were each lower, e.g., 1 ohm, because of greater forces concentrated on those sensors 33, the measured value of $R_{11}$ would be:

$$R_{11}=10(1+1+1)/(10+1+1+1)=30/13=2.31 \text{ ohms, i.e., a}$$
value of about 77 percent below the actual value of $R_{11}$.

Figure 10B:
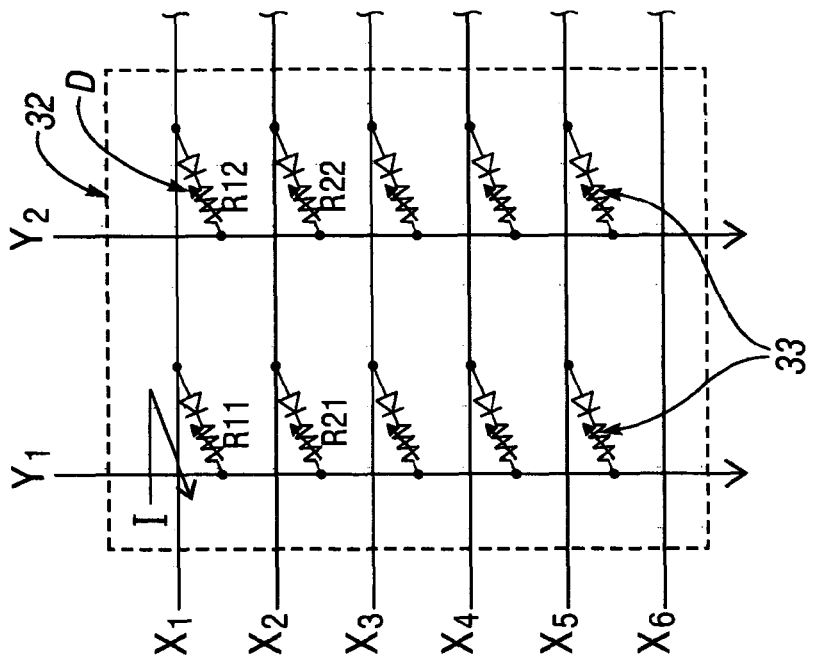
FIG. 10B is a view similar to that of FIG. 10A, but showing sensors modified to include a diode junction.
Figure 10A:
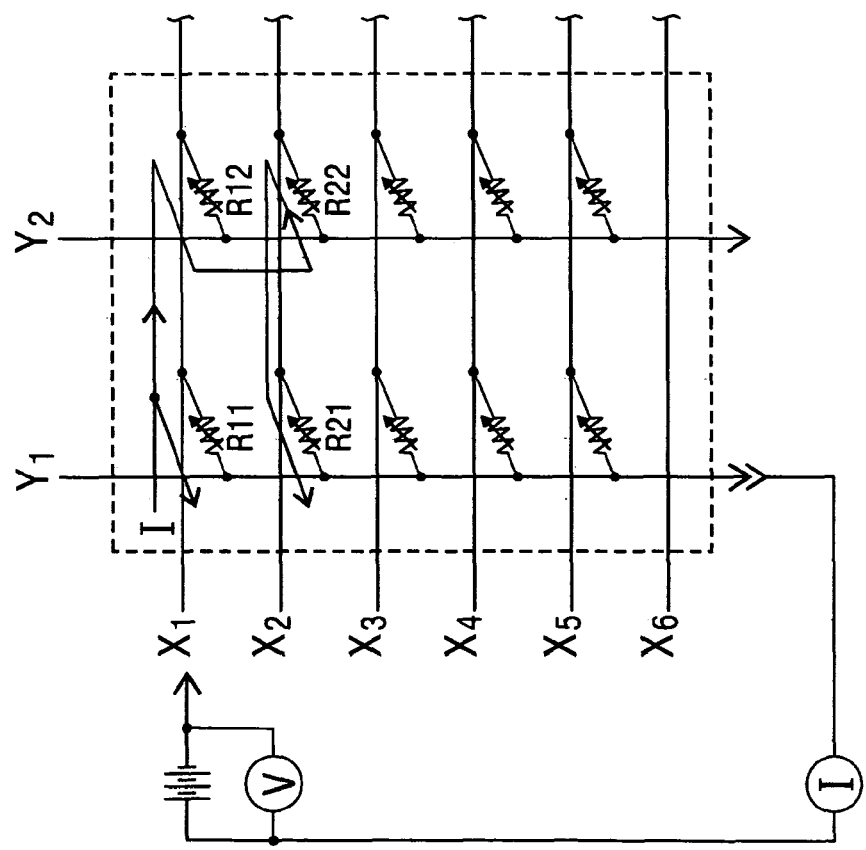
FIG. 10A is a schematic diagram showing a six row by two column matrix of the sensors of FIG. 5.

On the other hand, by placing a diode in series with each piezoresistive sensor element 33, as shown in FIG. 10B, the electrical resistance of an element measured in a reverse, counterclockwise direction a test current flow through the sensor element, e.g., $R_{22}$, would be for practical purposes arbitrarily large, or infinity compared to the clockwise forward paths of current through the other resistances shown in FIGS. 10A and 10B. In this case, the measured resistance value for a 2×2 matrix of four resistances each having a value of 10 ohms would be:

$$R_{x1y1}=10(1+\infty+1)/(10+1+\infty+1)=10 \text{ ohms, the correct value.}$$

Thus, modifying each sensor 33 element to include a p-n junction thereby give the sensor element a diode-like characteristic electrically isolates, i.e., prevents backward current flow, through each sensor element 33. This enables the correct value of electrical resistance of each sensor element 33 and hence forces exerted thereon to be measured accurately $R_{x1}Y_1$ using row and column matrix addressing rather than requiring a separate pair of conductors for each sensor element.

The above-described components of force minimization apparatus 20 according to the present invention are interconnected to form a closed-loop servo control system. That system is effective in reducing body force concentrations using an algorithm according to the method of the present invention. An understanding of this method and apparatus may be facilitated by referring to FIG. 11, which is a block diagram of an electro-pneumatic controller system components 20A of apparatus 20, in conjunction with the diagrammatic view of the apparatus shown in FIG. 1, and the perspective view shown in FIG. 5.

Figure 11:
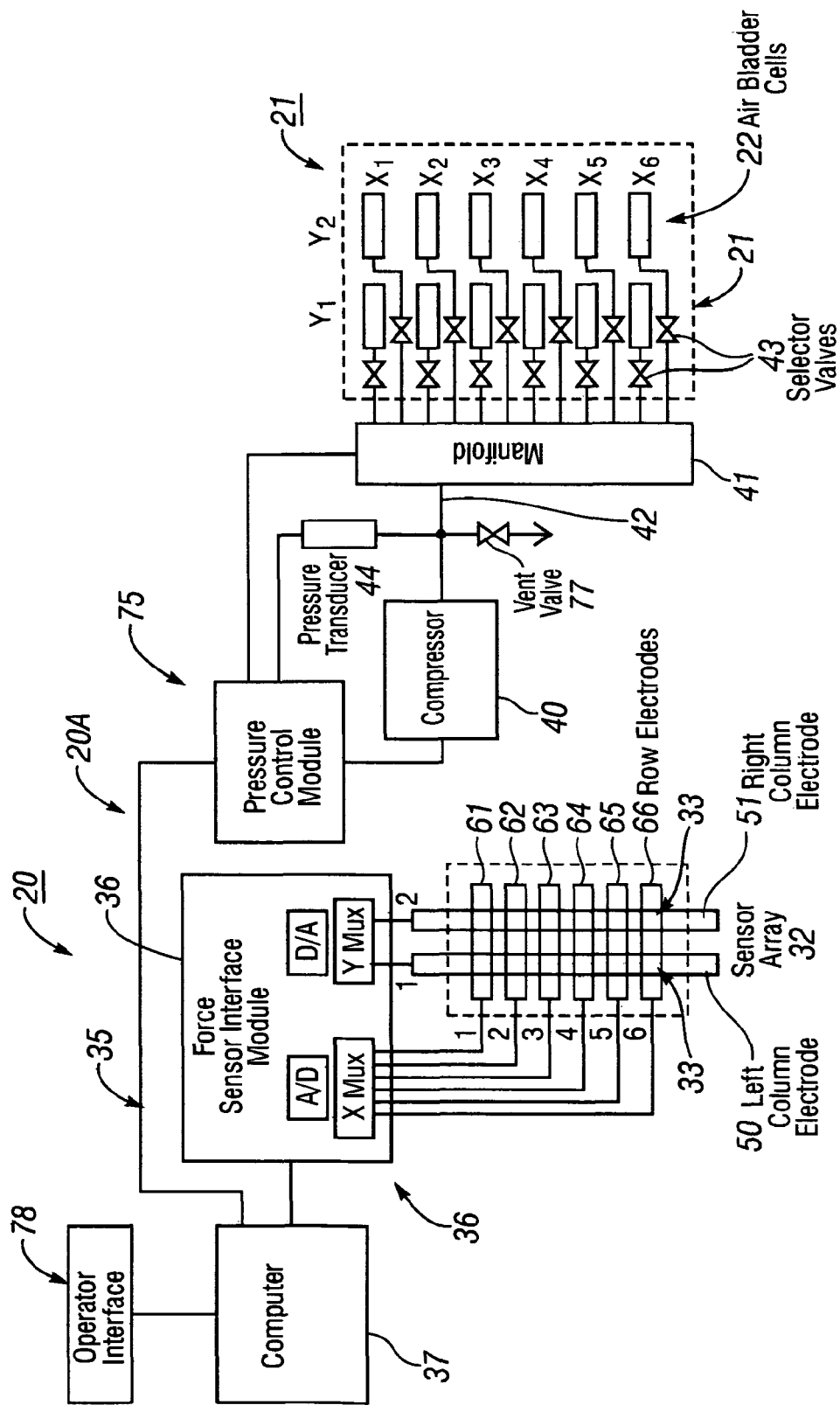
FIG. 11 is a block diagram of electro-pneumatic controller elements of the apparatus of FIG. 1.

Referring to FIG. 11, it may be seen that electro-pneumatic controller apparatus 20A includes a computer 37 which is bidirectionally coupled to force sensor array 32 through force sensor interface module 36. The sensor interface module 36 includes a Digital-to-Analog Converter (DAC) 71 for generating in response to control signals from computer 37 test voltages or currents which are directed to matrix-addressed individual force sensors 33.

Individual force sensors 33 are addressed by connecting one terminal of a current or voltage source controlled by DAC 71 to a selected one of X-row conductors 1-6 by an X multiplexer 72, and connecting the other terminal of the source to a selected one of Y-column conductors 1 or 2 by a Y multiplexer 73. Sensor interface module 37 also included an Analog-to-Digital Converter (ADC) 74 which measures the voltage drop or current through a sensor 33 resulting from application of a test current or voltage, and inputs the measured value to computer 37. Using predetermined scale factors, computer 37 calculates the instantaneous value of electrical resistance of a-selected addressed sensor 33, and from that resistance value, a corresponding normal force instantaneously exerted on the addressed sensor.

In response to control signals cyclically issued by computer 37, X multiplexer 72 and Y multiplexer 73 are used to cyclically measure the resistance of each force sensor element 33, at a relatively rapid rate of, for example, 3,000 samples per second, enabling computer 37 to calculate the force exerted on each force sensor 33 at that sampling rate.

Referring still to FIG. 11, apparatus 20 includes a pressure control module 75 for dynamically controlling the air pressure in each individual air bladder cell 22, in response to command signals issued by computer 37, based 'upon values of force measured by sensor array 32 and an algorithm programmed in the computer. As shown in FIG. 11, pressure control module 75 is operably interconnected to air compressor 40 and air pressure transducer 44 at output port 76 of the compressor to pressurize air in the outlet port to a value controllable by computer 37.

Outlet port 76 of compressor 40 is coupled to inlet port 42 of a 12-outlet port manifold 41. In response to electrical control signals issued by computer 37 and routed through pressure control module 75, each of 12 individual air bladder cell inlet selector valves 43 connected to separate outlet ports 43A of manifold 41 is individually controllable.

In a first, open position of a selector valve 43, the air inlet port 31 of a selected air bladder cell 22 is pressurized to a pressure measured by transducer 44 to a predetermined value, by turning on compressor 40, to thereby inflate the cell to a desired pressure. Alternatively, with compressor 40 in an off-mode, a vent valve 77 coupled to the input port 42 of manifold 41 may be opened to deflate an air bladder cell 22 to a lower pressure value by exhausting air to the atmosphere.

After a selected one of the 12 selector valves 43 has been opened in response to a command signal from computer 37 for a time period sufficient to inflate a selected air bladder cell 22 to a predetermined pressure, an electrical signal output by pressure transducer 44, which is proportional to the pressure in that cell and input to computer 37, results in the computer outputting a closure command signal to the valve and a shut-off command signal to compressor 40.

When a selected selector valve 43 and vent valve 77 have been opened in response to command signals from computer 37 to deflate a selected air bladder cell 22 to a lower predetermined pressure, an electrical signal from pressure transducer 44 input to computer 37 results in an electrical closure command signal being output from the computer. That command signal closes vent valve 77 and the open selector valve 43, thereby maintaining the selected lower pressure in the selected air bladder cell. In an exactly analogous fashion, the air pressure in each other air bladder cell 22 is sequentially adjustable by sending a command signal to a selector valve 43 to open that valve, and operating compressor 40 and/or vent valve 77 to inflate or deflate the air bladder cell to a predetermined pressure.

Figure 12:
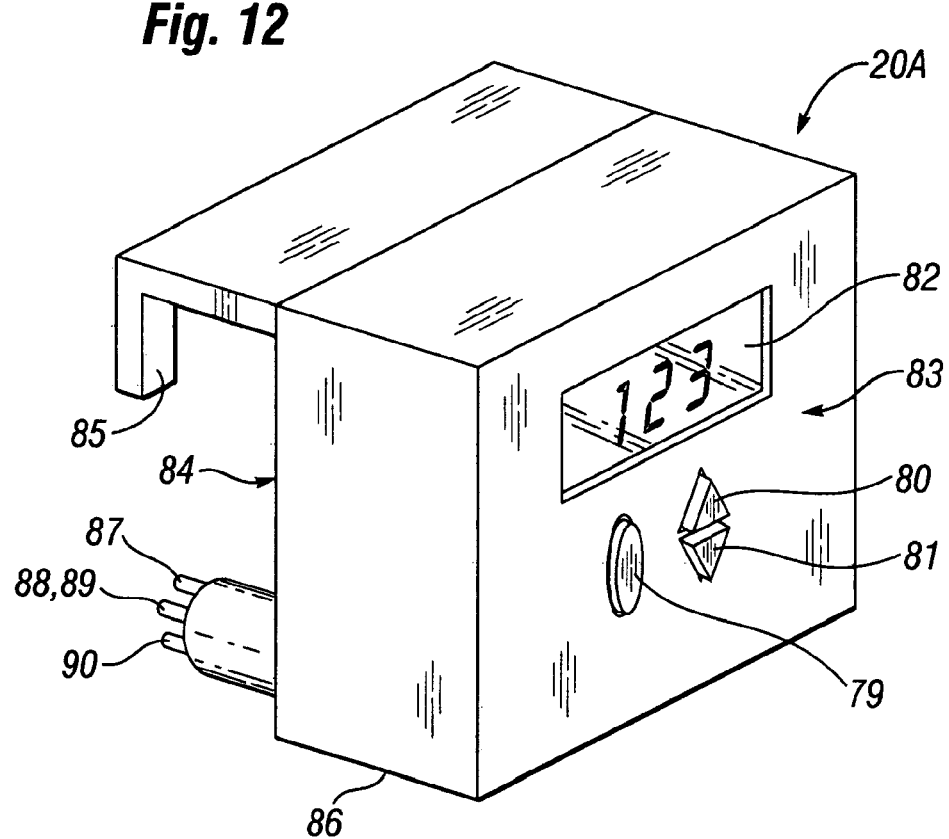
FIG. 12 is a simplified perspective view of the electro-pneumatic controller of FIG. 11.

FIG. 12 is a simplified perspective view of a preferred embodiment of an enclosure for electro-pneumatic apparatus 20A shown in FIG. 11 and described above. As shown in FIGS. 11 and 12, electro-pneumatic controller 20A includes an operator interface module 78. Operator interface module includes manual controls, including a multi-function, on/off, mode control switch and button 79, up and down data entry slewing buttons 80, 81, and a digital display 82. Display 82 is controllable by switch 99 to selectively display air pressure within and force on selectable air bladder cells 22, and the sum and average of all forces exerted on sensors 33.

As shown in FIG. 12, electro-pneumatic controller 20A is preferably contained in a box-like enclosure 83 which has protruding from a rear panel 84 thereof an L-bracket 85 for suspending the enclosure from a side board or end board of a bed. Enclosure 83 of electro-pneumatic controller 20A also includes a tubular member 86 for interfacing air hoses 87 with air bladder cells 22, row and column conductors 88, 89, to sensors 33 of sensor array 32, and an electrical power cord 90 to a source of electrical power for powering the components of apparatus 20A.

Force Minimization Algorithm

The force minimization apparatus described above is made up of a multiplicity of air bladder cells 22. Each cell 22 has on its upper surface a separate force sensor 33. An air pressure transducer 44 is provided to measure the air pressure in each cell. Each force sensor is located in a potential contact region between a person lying on cushion 21 and the air bladder cell. Each piezoresistive force sensor 33 functions as a force sensitive transducer which has an electrical resistance that is inversely proportional to the maximum force exerted by a person's body on the air bladder cell 22, the maximum force corresponding to the lowest resistance path across any part of each sensor.

As shown in FIG. 3, each air bladder cell 22 supports a different longitudinal zone of the user such as the head, hips or heels. The compressor 40 and selector valves 43 controlling the air pressure in each zone are controlled by force sensors 33 and pressure measurements made by pressure transducer 44, using a novel algorithm implemented in computer 37.

There can be a minimum of one zone using one air bladder cell 33, and up to N zones using n air bladder cells, wherein each zone has a force sensor 33 to measure the maximum force on that air bladder cell, the pressure transducer 44 being used to measure the air pressure in that air bladder cell. The control algorithm is one of continuous iteration wherein the force sensors 33 determine the peak force on the patient's body, and the pressure transducer 44 measures the pressure at which the force occurs. At the end of a cycle sampling forces on all sensors, the bladder air pressure is restored to the pressure where the force was minimized for all zones. This process continues and the apparatus constantly hunts to find the optimal bladder pressures for each individual cell resulting in minimizing peak forces on a person supported by overlay cushion 21.

Algorithm Description

Given:

N Zones each containing one air bladder cell and numbered one to N

The air bladder cell of each zone is selectably connectable to an air pressure transducer to measure P#.

Each air bladder cell is fitted with an individual force sensor capable of measuring the maximum force F# exerted on the surface of each cell.

A common compressor supplies air at pressures of up to 5 psi to selected individual air bladder cells of the zones. There is a normally closed vent valve for deflating a selected air bladder cell by exhausting air to the atmosphere through the vent valve.

There is a selector valve that selects which air bladder is being inflated with air or deflated by exhausting air to the atmosphere through the vent valve.

Algorithm Steps

1. Set: Pset, start, close vent valve
1A. Set: i=1
2. Select zone i by opening selector valve i
3. Turn the compressor on.
4. Measure the air pressure in the air bladder cell in zone i
5. Pressurize the zone i air bladder cell to Pset
6. Increment i by 1 and repeat steps 2-5 until i=N
7. Set: i=1 and select zone i
8. Obtain the force sensor readings for all zones.
9. Open Vent valve.
10. Deflate the zone i air bladder cell to a predetermined minimum pressure and monitor all the force sensor readings on all air bladder cells. Maintain bladder pressures in all other air bladder cells at Pset.

11. Measure forces on all air bladder cells as the single, zone i air bladder is being deflated and compute the sum and optionally the average of all force sensor readings 12. Store in computer memory the pressure reading of the zone i air bladder cell at which the minimum sum and optionally the average of all force sensor readings occurs.

13. Restore the pressure in the zone i air bladder cell to the value where the minimum sum and average force sensor readings for all the force sensors was obtained.

14. Close the zone i selector valve. Maintain the pressure in zone i

15. Increment i by 1

16. Repeat steps 8 thru 15 until i=N.

17. Reduce Pset.

18. Repeat Steps 1A thru 16 (i.e., with a reduced Pset). Caveat

19. Constantly monitor all force sensors and if significant change (Delta F>0.2*F#) is detected (patient moved) start over at Step 1.

Figure 13:
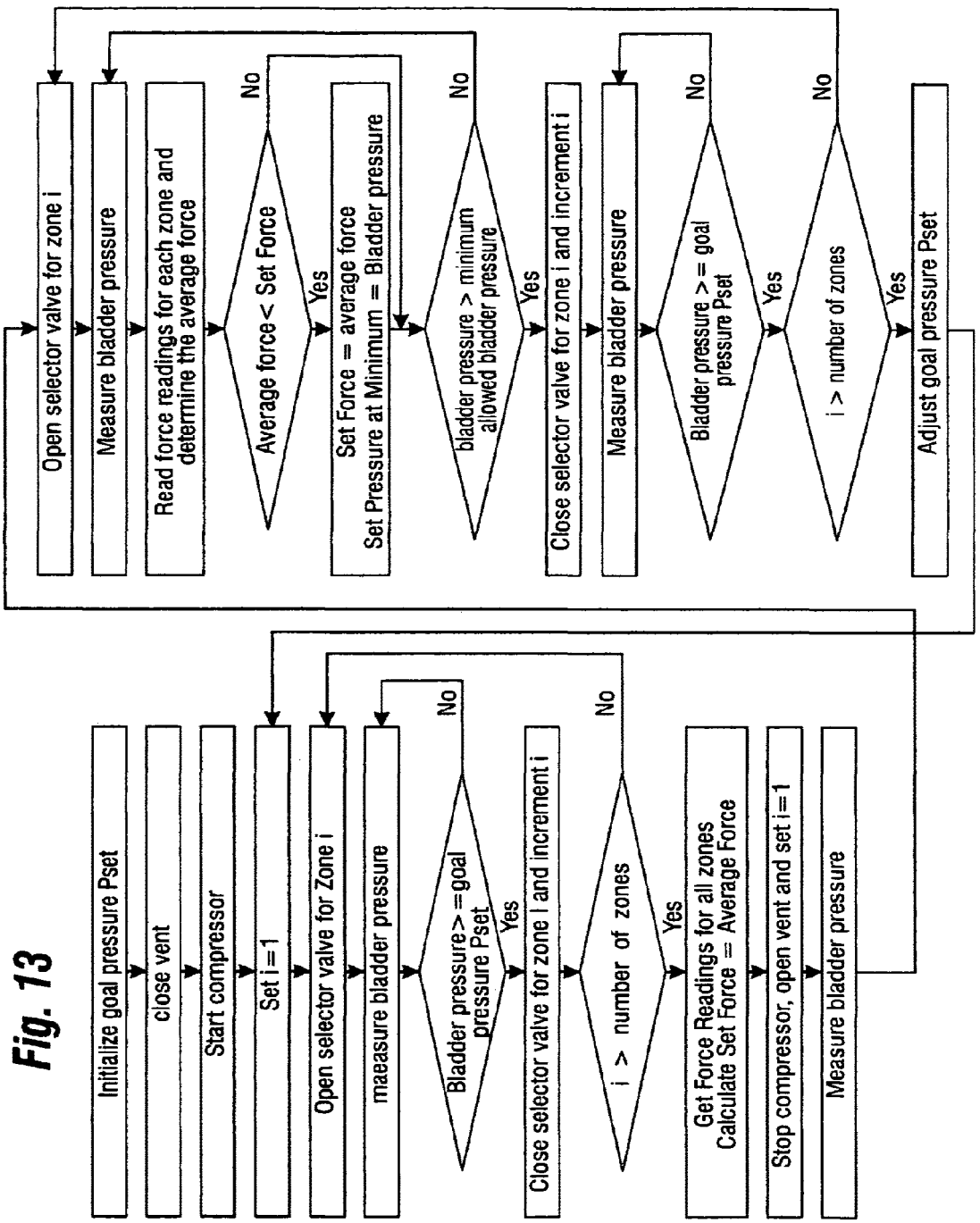
FIG. 13 is a flow chart showing operation of the apparatus of FIG. 1.

FIG. 13 is a flow chart showing the operation of apparatus 20 utilizing the algorithm described above. Table 1 lists appropriate lower and upper initial set pressures for bladders 22, as a function of the weight of a patient or other person supported by overlay cushion 21 of the apparatus.

TABLE 1

| Patient Weight | Minimum Pressures | Start Pressure |
|---|---|---|
| 75-119 Pounds | 5.5" ± 0.7: $H_2O$ | 6.5" ± 0.7: $H_2O$ |
|  | 10.31 ± 2 mm Hg | 12.18 ± 2 mm Hg |
| 120-164 Pounds | 6" ± 0.7: $H_2O$ | 8" ± 0.7: $H_2O$ |
|  | 11.25 ± 2 mm Hg | 15 ± 2 mm Hg |
| 165-199 Pounds | 8" ± 0.7: $H_2O$ | 10" ± 0.7: $H_2O$ |
|  | 15 ± 2 mm Hg | 18.75 ± 2 mm Hg |
| 200-250 Pounds | 10 ± 0.7: $H_2O$ | 12" ± 0.7: $H_2O$ |
|  | 18.75 ± 2 mm Hg | 22.49 ± 2 mm Hg |
| Maximum Pressure |  | 26" ± 0.7: $H_2O$ |
|  |  | 48.74 ± 4 mm Hg |

In a variation of the method and apparatus according to the present invention and described above, after the pressures in each air bladder cell have been optimized for minimum force concentration, inlet tubes 31 could be permanently sealed, and the adaptive cushion 21 permanently disconnected from pressure control module 75. This variation would also enable the custom fabrication of cushions 21 using air bladder cells 22, for customizing chair cushions to minimize force concentrations on a particular individual. Similarly, the variation of the method and apparatus according to the present invention could be used to customize saddle cushions or car seats.

What is claimed is:

1. A method for reducing the magnitude of interface pressure exerted on parts of a human body in response to contact with a supporting object, said method comprising the steps of;
   a. providing a cushion for placement between a supporting object and a human body, said cushion having at least first and second hermetically sealable air bladder cells each made of a thin, flexible, air impervious material,
   b. providing at least first and second force sensors associated with said first and second air bladder cells, respectively, each of said force sensors having an electrical characteristic which varies in a predetermined way with a force exerted on said first and second air bladder cells, respectively by said body,
   c. providing a source of pressurized gas for pressurizing a hollow interior space of each said air bladder cells to an individually controllable pressure,
   d. providing at least one pressure sensitive transducer operatively coupleable to each of said air bladder cells to thereby measure gas pressures within said hollow interior spaces of each said air bladder cells,
   e. providing a control apparatus for receiving signals from said force sensors and said pressure transducer and for controlling said source of pressurized gas,
   f. receiving at said control apparatus a signal from said pressure transducer representative of said gas pressure within said hollow interior space of a said air bladder cell,
   g. receiving at said control apparatus signals from said first and second force sensors representative of forces exerted on said first and second said air bladder cells,
   h. calculating a first sum of forces from said first and second force sensors obtained while the first and second air bladder cells are inflated at first and second gas pressures, respectively,
   i. varying the gas pressure in the first individual air bladder cell to a new pressure,
   j. calculating a second sum of forces from said first and second force sensors obtained while the first air bladder cell is inflated to the new pressure,
   k. determining within said control apparatus the smaller of the first and second sum of forces; and
   l. using said transducer signals and said force sensor signals to calculate within said control apparatus appropriate pressurization values for said hollow interior spaces of said air bladder cells which correspond to the smaller of the first and second sum of forces, and
   m. providing from said control apparatus a control signal to said source of pressurized gas to thereby pressurize said hollow interior spaces of a said air bladder cells to the appropriate pressurization values.

2. The method of claim 1 wherein said cushion is further defined as including in addition to said first and second air bladder cells an additional p−2 air bladder cells, where p is an integer greater than 3.

3. The method of claim 2 further including an additional p−2 force sensors each of which is associated with one of said additional p−2 air bladder cells.

4. A method of controlling gas pressure comprising:
   providing a cushion for placement between a supporting object and a person, said cushion having at least first and second hermetically sealable bladders;
   providing at least first and second interface pressures sensors associated with said first and second bladders, respectively, each of said interface pressure sensors having an electrical characteristic which varies in a predetermined way with an interface pressure exerted on said first and second bladders, respectively;
   providing at least one gas pressure sensor operatively coupleable to each of said bladders to thereby measure gas pressures within the first and second bladders,
   providing a control apparatus configured to perform the following:
   measuring a first interface pressure between the person and the first bladder using the first interface pressure sensor while the first bladder is inflated at a first gas pressure;
   measuring a second interface pressure between the person and the second bladder using the second interface pressure sensor while the first bladder is inflated at the first gas pressure;
   calculating a first sum of the first measured and second measured interface pressures;
   changing the gas pressure of the first bladder to a second gas pressure different from the first gas pressure;

re-measuring the first interface pressure between the person and the first bladder using the first interface pressure sensor while the first bladder is inflated at the second gas pressure;

re-measuring the second interface pressure between the person and the second bladder using the second interface pressure sensor while the first bladder is inflated at the second gas pressure;

calculating a second sum of the first re-measured and second re-measured interface pressures;

comparing the first sum to the second sum; and changing the gas pressure inside the first bladder based on the comparison of the first sum to the second sum.

5. The method of claim 4 wherein the second gas pressure is less than the first gas pressure, and the method further comprises changing the gas pressure of the first bladder to a third gas pressure that is less than the second gas pressure if the second sum is less than the first sum.

6. The method of claim 5 further comprising:
(a) re-measuring the first interface pressure between the person and the first bladder using the first interface pressure sensor while the first bladder is inflated to the third gas pressure;
(b) re-measuring the second interface pressure between the person and the second bladder using the second interface pressure sensor while the first bladder is inflated to the third pressure;
(c) calculating a third sum of the re-measured interface pressures from steps (a) and (b);
(d) comparing the third sum to the second sum; and
(e) changing the gas pressure inside the first bladder to a fourth gas pressure less than the third gas pressure if the third sum is less than the second sum.

7. The method of claim 6 further comprising changing the gas pressure inside the first bladder back to the second gas pressure if the third sum is greater than the second sum.

8. The method of claim 4 wherein the second gas pressure is greater than the first gas pressure and the method further comprises changing the gas pressure of the first bladder to a third gas pressure that is greater than the second gas pressure if the second sum is less than the first sum.

9. The method of claim 4 further comprising:
measuring an additional interface pressure between the person and an additional bladder using an additional interface pressure sensor while the first bladder is inflated at the first gas pressure;
including the additional interface pressure in the first sum;
re-measuring the additional interface pressure between the person and the additional bladder using the additional interface pressures sensor while the first bladder is inflated at the second gas pressure; and
including the additional re-measured interface pressure in the second sum.

10. The method of claim 4 wherein the supporting object is a bed.

11. The method of claim 4 wherein the first and second interface pressure sensors are included in a force sensing layer on top of the cushion.

12. The method of claim 4 further comprising:
monitoring changes in the first and second interface pressures;
comparing the changes to a threshold; and
restarting the method if the changes exceed the threshold.

13. A method of controlling gas pressure comprising:
providing a cushion for placement between a supporting object and a person, said cushion having a plurality of hermetically sealable bladders;
providing a plurality of interface pressures sensors associated with the plurality of bladders, each of said interface pressure sensors having an electrical characteristic which varies in a predetermined way with an interface pressure exerted on the respective bladders;
providing at least one gas pressure sensor operatively coupleable to each of said bladder to thereby measure gas pressures within each of the plurality of bladders,
providing a control apparatus configured to perform the following:
setting a gas pressure inside of a selected one of the plurality of bladders to a first gas pressure;
determining a first sum of interface pressures between the person and each one of the plurality of bladders using the plurality of interface pressure sensors while the gas pressure inside the selected bladder is at the first gas pressure;
changing gas pressure inside of the selected bladder to a second gas pressure;
determining a second sum of interface pressures between the person and each one of the plurality of bladders using the plurality of interface pressure sensors while the selected bladder is at the second gas pressure;
comparing the first sum to the second sum;
changing the gas pressure of the selected bladder back to the first gas pressure if the second sum is greater than the first sum; and
changing the gas pressure of the selected bladder to a third pressure different from the second pressure if the second sum is less than the first sum.

14. The method of claim 13 wherein the second gas pressure is less than the first gas pressure.

15. The method of claim 13 further comprising:
determining a third sum of interface pressures between the person and each one of the plurality of bladders using the plurality of interface pressure sensors while the selected bladder is at the third gas pressure;
comparing the second sum to the third sum;
changing the gas pressure of the selected bladder back to the second gas pressure if the third sum is greater than the second sum; and
changing the gas pressure of the selected bladder to a fourth pressure different from the third pressure if the third sum is less than the second sum.

16. The method of claim 13 wherein the supporting object is a bed.

17. The method of claim 13 wherein the plurality of interface pressure sensors are included in a pressure sensing layer on top of the cushion.

18. A method of controlling gas pressure comprising:
providing a cushion for placement between a supporting object and a person, said cushion having at least first and second hermetically sealable bladders;
providing at least first and second interface pressures sensors associated with said first and second bladders, respectively, each of said interface pressure sensors having an electrical characteristic which varies in a predetermined way with an interface pressure exerted on said first and second bladders, respectively;
providing at least one gas pressure sensor operatively coupleable to each of said bladder to thereby measure gas pressures within the first and second bladders,
providing a control apparatus configured to perform the following:
setting a gas pressure inside the first and second bladders to a first gas pressure;

measuring a first interface pressure between the person and the first bladder using the first interface pressure sensor while the first bladder is inflated at the first gas pressure;

measuring a second interface pressure between the person and the second bladder using the second interface pressure sensor while the second bladder is at the first gas pressure;

determining which of the first and second interface pressures is greater;

identifying which of the first and second bladders has the greater of the first and second interface pressures (the greater bladder) and which of the first and second bladders has the lesser of the first and second interface pressures (the lesser bladder);

changing gas pressure inside the greater bladder from the first gas pressure to a second gas pressure;

measuring a third interface pressure between the person and the greater bladder while the greater bladder is inflated at the second gas pressure;

measuring a fourth interface pressure between the person and the lesser bladder while the lesser bladder is inflated at the first gas pressure;

calculating a first sum of the first and second measured interface pressures;

calculating a second sum of the third and fourth measured interface pressures; and changing gas pressure inside the greater bladder based on the comparison of the first sum to the second sum.

19. The method of claim 18 further comprising:

changing the gas pressure of the greater bladder back to the first gas pressure if the second sum is greater than the first sum; and changing the gas pressure of the greater bladder to a third pressure different from the second pressure if the second sum is less than the first sum.

20. The method of claim 18 wherein the supporting object is a bed.

21. The method of claim 18 wherein the first and second interface pressure sensors are included in a pressure sensing layer on top of the cushion.

22. The method of claim 18 further comprising:

monitoring changes in the first and second interface pressures;

comparing the changes to a threshold; and restarting the method if the changes exceed the threshold.

23. The method of claim 18 further comprising:

measuring an additional interface pressure between the person and an additional bladder while the additional bladder and the lesser bladder are inflated at the first gas pressure; and including the additional interface pressure in the second sum.

* * * * *